US009676843B2

United States Patent
Demuth et al.

(10) Patent No.: US 9,676,843 B2
(45) Date of Patent: Jun. 13, 2017

(54) USES OF ANTIBODIES DIRECTED AGAINST AMYLOID-β

(71) Applicant: Probiodrug AG, Halle/Saale (DE)

(72) Inventors: Hans-Ulrich Demuth, Halle/Saale (DE); Stephan Schilling, Halle/Saale (DE); Martin Kleinschmidt, Halle/Saale (DE); Kathrin Gnoth, Halle/Saale (DE); Anita Reisenauer-Schaupp, Baienfurt (DE); Jens-Ulrich Rahfeld, Lieskau (DE); Sonja Kampfer, Germering (DE)

(73) Assignee: PROBIODRUG AG, Halle (Saale) (DE)

( * ) Notice: Subject to any disclaimer, the term of this patent is extended or adjusted under 35 U.S.C. 154(b) by 0 days.

(21) Appl. No.: 14/844,726

(22) Filed: Sep. 3, 2015

(65) Prior Publication Data

US 2016/0053001 A1    Feb. 25, 2016

Related U.S. Application Data

(62) Division of application No. 13/252,929, filed on Oct. 4, 2011, now Pat. No. 9,156,907, which is a division of application No. 12/500,940, filed on Jul. 10, 2009, now Pat. No. 8,058,405.

(60) Provisional application No. 61/082,309, filed on Jul. 21, 2008.

(51) Int. Cl.
*A61K 39/395* (2006.01)
*C07K 16/18* (2006.01)
*G01N 33/68* (2006.01)
*A61K 39/00* (2006.01)

(52) U.S. Cl.
CPC ......... *C07K 16/18* (2013.01); *G01N 33/6896* (2013.01); *A61K 39/3955* (2013.01); *A61K 2039/505* (2013.01); *C07K 2317/24* (2013.01); *C07K 2317/34* (2013.01); *C07K 2317/56* (2013.01); *C07K 2317/92* (2013.01); *G01N 2333/4709* (2013.01); *G01N 2800/2814* (2013.01); *G01N 2800/2821* (2013.01); *G01N 2800/387* (2013.01)

(58) Field of Classification Search
CPC .......... A61K 39/3955; A61K 2039/505; C07K 16/18; C07K 2317/56; C07K 2317/34; C07K 2317/24; C07K 2317/622; C07K 2317/626; G01N 33/6896; G01N 2333/4709; G01N 2800/2821; G01N 2800/387; G01N 2800/2814
See application file for complete search history.

(56) References Cited

U.S. PATENT DOCUMENTS

| 7,122,374 | B1 | 10/2006 | Saido et al. |
|---|---|---|---|
| 7,381,801 | B2 | 6/2008 | Renner et al. |
| 2003/0165496 | A1 | 9/2003 | Basi et al. |
| 2004/0241164 | A1 | 12/2004 | Bales et al. |
| 2004/0265919 | A1 | 12/2004 | Vanderstichele et al. |
| 2005/0009150 | A1 | 1/2005 | Basi et al. |
| 2005/0058635 | A1 | 3/2005 | Demuth et al. |
| 2006/0073149 | A1 | 4/2006 | Bales et al. |

FOREIGN PATENT DOCUMENTS

| EP | 1911765 A2 | 4/2008 |
|---|---|---|
| JP | 2005/527199 | 9/2005 |
| JP | 2006/513259 | 4/2006 |
| JP | 2007/525160 | 9/2007 |
| WO | WO 03/070760 A2 | 8/2003 |
| WO | WO 2004/013172 | 2/2004 |
| WO | WO 2004/032868 A2 | 4/2004 |
| WO | WO 2004/080419 | 9/2004 |
| WO | WO 2007/068412 A2 | 6/2007 |
| WO | WO 2008/060364 A2 | 5/2008 |

OTHER PUBLICATIONS

Bard et al. Nat Med. 2000, 6(8):916-919.*
DeMattos et al. Proc Natl Acad Sci USA, 2001, 98(15):8850-8855.*
Geddes et al. Neurobiol. Aging 1999, 20:75-79.*
Hampel et al. Progress Neurobiol. 2011, 95:718-728.*
Lee et al. J. Biol. Chem. Feb. 2006; 281(7):4292-4299.*
Lemere et al. Rejuvenation Res. 2006; 9(1):77-84.*
Lin et al. Diabetes, 2007, 56:1324-1332.*
Perez-Garmendia et al. J. Neuroimmunol. 2010, 229:248-255.*
Vickers JC. Drugs Aging. 2002; 19(7):487-494.*
Frenkel et al., Generation of anti-β-amyloid antibodies via phage display technology, Vaccine, 2004, pp. 2505-2508, vol. 22.
Immuno-Biological Laboratories Co., Amyloid β ELISA Kits, Product literature, Ltd., 2008, 1 page.
Immuno-Biological Laboratories Co., Antibodies to Amyloid β, Product literature, Ltd., 2008, 1 page.
Japanese Office Action in corresponding Japanese Application No. 2011-519110 dated Jan. 21, 2014, in English, 5 pages.
Johnson-Wood et al., Amyloid precursor protein processing and Abeta42 deposition in a transgenic mouse model of Alzheimer disease, Proc Natl Acad Sci USA, 1997, vol. 94, pp. 1550-1555.
Lin et al., Determination of Binding Constant and Stoichiometry for Antibody-Antigen Interaction with Surface Plasmon Resonance, Current Proteomics, 2006, pp. 271-282, vol. 3.
Saido et al., Amino- and carboxyl-terminal heterogeneity of β-amyloid peptides deposited in human brain, Neuroscience Letters, 1996, pp. 173-176, vol. 215.

(Continued)

*Primary Examiner* — Kimberly A. Ballard
(74) *Attorney, Agent, or Firm* — Dentons US LLP

(57) ABSTRACT

Diagnostic assays for the diagnosis of amyloidosis, in particular Alzheimer's disease, and related aspects. In particular, monoclonal antibodies and an antibody assay are provided.

26 Claims, 11 Drawing Sheets

(56) References Cited

OTHER PUBLICATIONS

Schilling et al., Inhibition of glutaminyl cyclase prevents pGlu-Aβ formation after intracortical/hippocampal microinjection in vivo/in situ, J. Neurochem., 2008, pp. 1225-1236, vol. 106.
The Genetics Company, Inc., for the Selective and Quantitative Measurement of Amyloid Beta x-40 and x-42 Peptides: -Monoclonal Antibodies -High Sensitivity ELISA Kits, -Brain Tissue ELISA Kits, Prospectus, Nov. 2008, 16 pages.

\* cited by examiner

USES OF ANTIBODIES DIRECTED AGAINST AMYLOID-β

CROSS-REFERENCE TO RELATED APPLICATIONS

This application is a Divisional of U.S. application Ser. No. 13/252,929, filed Oct. 4, 2011 which is a Divisional of U.S. application Ser. No. 12/500,940, filed Jul. 10, 2009, issued as U.S. Pat. No. 8,058,405 on Nov. 11, 2011, which claims priority to U.S. Provisional Application No. 61/082,309 filed on Jul. 21, 2007; all are incorporated herein by reference in their entireties for all purposes.

INCORPORATION-BY-REFERENCE OF MATERIAL SUBMITTED IN COMPUTER READABLE FORMAT (CRF)

The Sequence Listing, which is a part of the present disclosure, includes a computer readable form comprising nucleotide and/or amino acid sequences of the present invention. The subject matter of the Sequence Listing is incorporated herein by reference in its entirety.

INCORPORATION-BY-REFERENCE OF DEPOSITED BIOLOGICAL MATERIAL

The following biological material, which is a part of the present disclosure, has been deposited in accordance with the Budapest Treaty and are available at the Deutsche Sammlung für Mikroorganismen and Zellkulturen (DSMZ), Inhoffenstr. 7b, 38124 Braunschweig, DE: hybridoma cell line 5-5-6, Deposit No. DSM ACC 2923, deposit date Jun. 17, 2008; hybridoma cell line 6-1-6, Deposit No. DSM ACC 2924, deposit date Jun. 17, 2008; hybridoma cell line 17-4-3, Deposit No. DSM ACC 2925, deposit date Jun. 17, 2008; and hybridoma cell line 24-2-3, Deposit No. DSM ACC 2926, deposit date Jun. 17, 2008. Such hybridoma cell lines can produce monoclonal antibodies specifically recognizing Aβ N3pE-x. The deposited biological material described above is incorporated herein by reference in its entirety.

FIELD OF THE INVENTION

The present invention pertains to novel diagnostic assays for the diagnosis of amyloidosis, a group of disorders and abnormalities associated with amyloid protein such as Alzheimer's disease and related aspects. In particular, an antibody assay is provided.

BACKGROUND OF THE INVENTION

Amyloidosis is not a single disease entity but rather a diverse group of progressive disease processes characterized by extracellular tissue deposits of a waxy, starch-like protein called amyloid, which accumulates in one or more organs or body systems. As the amyloid deposits accumulate, they begin to interfere with the normal function of the organ or body system. There are at least 15 different types of amyloidosis. The major forms are primary amyloidosis without known antecedent, secondary amyloidosis following some other condition, and hereditary amyloidosis.

Secondary amyloidosis occurs during chronic infection or inflammatory disease, such as tuberculosis, a bacterial infection called familial Mediterranean fever, bone infections (osteomyelitis), rheumatoid arthritis, inflammation of the small intestine (granulomatous ileitis), Hodgkin's disease and leprosy.

Amyloid deposits include amyloid P (pentagonal) component (AP), a glycoprotein related to normal serum amyloid P (SAP), and sulphated glycosaminoglycans (GAG), complex carbohydrates of connective tissue. Amyloid protein fibrils, which account for about 90% of the amyloid material, comprise one of several different types of proteins. These proteins are capable of folding into so-called "beta-pleated" sheet fibrils, a unique protein configuration which exhibits binding sites for Congo red resulting in the unique staining properties of the amyloid protein.

Many diseases of aging are based on or associated with amyloid-like proteins and are characterized, in part, by the buildup of extracellular deposits of amyloid or amyloid-like material that contribute to the pathogenesis, as well as the progression of the disease. These diseases include, but are not limited to, neurological disorders such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome, Lewy body dementia, hereditary cerebral hemorrhage with amyloidosis (Dutch type); the Guam Parkinson-Dementia complex. Other diseases which are based on or associated with amyloid-like proteins are progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

Although pathogenesis of these diseases may be diverse, their characteristic deposits often contain many shared molecular constituents. To a significant degree, this may be attributable to the local activation of pro-inflammatory pathways thereby leading to the concurrent deposition of activated complement components, acute phase reactants, immune modulators, and other inflammatory mediators (McGeer et al., Tohoku J Exp Med. 174(3): 269-277 (1994)).

Recently, accumulating evidence demonstrates involvement of N-terminal modified Aβ peptide variants in Alzheimer's disease. Aiming biopsies display a presence of Aβ 1-40 and Aβ 1-42 not only in the brain of Alzheimer's patients but also in senile plaques of unaffected individuals. However, N-terminal truncated and pyroGlu modified Aβ N3pE-40/Aβ N3pE-42 is almost exclusively engrained within plaques of Alzheimer's disease patients, making this Aβ variant an eligible diagnostic marker and a potential target for drug development.

At present, several commercial manufacturers offer ELISA kits which allow a detection of Aβ 1-40/1-42 and Aβ N3pE-40/Aβ N3pE-42 in the low picogramm (pg) range.

The brains of Alzheimer's disease (AD) patients are morphologically characterized by the presence of neurofibrillary tangles and by deposits of Aβ peptides in neocortical brain structures (Selkoe, D. J. & Schenk, D. Alzheimer's disease: molecular understanding predicts amyloid-based therapeutics. Annu. Rev. Pharmacol. Toxicol. 43, 545-584 (2003)). Aβ peptides are liberated from the amyloid precursor protein (APP) after sequential cleavage by β- and γ-secretase. The γ-secretase cleavage results in the generation of Aβ 1-40 and Aβ 1-42 peptides, which differ in their C-termini and exhibit different potencies of aggregation, fibril formation and neurotoxicity (Shin, R. W. et al. Amyloid beta-protein (Abeta) 1-40 but not Abeta 1-42 contributes to the experimental formation of Alzheimer disease amyloid fibrils in rat brain. J. Neurosci. 17, 8187-8193 (1997); Iwatsubo, T. et al. Visualization of Abeta 42(43) and Abeta 40 in senile plaques with end-specific Abeta monoclonals: evidence that an initially deposited species is Abeta 42(43). Neuron 13, 45-53 (1994); Iwatsubo, T., Mann, D. M., Odaka, A., Suzuki, N. & Ihara, Y. Amyloid beta protein (Abeta) deposition: Abeta 42(43) precedes Abeta 40 in Down syndrome. Ann. Neurol. 37, 294-299 (1995); Hardy, J. A. & Higgins, G. A. Alzheimer's disease: the amyloid cascade hypothesis. Science 256, 184-185 (1992); Roβner, S., Ueberham, U., Schliebs, R., Perez-Polo, J. R. & Bigl, V. The regulation of amyloid precursor protein metabolism by cholinergic mechanisms and neurotrophin receptor signaling. Prog. Neurobiol. 56, 541-569 (1998)). In addition to C-terminal variability, N-terminally modified Aβ peptides are abundant (Saido, T. C. et al. Dominant and differential deposition of distinct beta-amyloid peptide species, A beta N3(pE), in senile plaques. Neuron 14, 457-466 (1995); Russo, C. et al. Presenilin-1 mutations in Alzheimer's disease. Nature 405, 531-532 (2000); Saido, T. C., Yamao, H., Iwatsubo, T. & Kawashima, S. Amino- and carboxyl-terminal heterogeneity of beta-amyloid peptides deposited in human brain. Neurosci. Lett. 215, 173-176 (1996)). It appears that a major proportion of the Aβ peptides undergoes N-terminal truncation by two amino acids, exposing a glutamate residue, which is subsequently cyclized into pyroglutamate (pE), resulting in Aβ(pE)-42 peptides (Saido, T. C. et al. Dominant and differential deposition of distinct beta-amyloid peptide species, A beta N3(pE), in senile plaques. Neuron 14, 457-466 (1995); Saido, T. C., Yamao, H., Iwatsubo, T. & Kawashima, S. Amino- and carboxyl-terminal heterogeneity of beta-amyloid peptides deposited in human brain. Neurosci. Lett. 215, 173-176 (1996)). Alternatively, pE may be formed following β'-cleavage by BACE1, resulting in Aβ N11(pE)-42 (Naslund, J. et al. Relative abundance of Alzheimer A beta amyloid peptide variants in Alzheimer disease and normal aging. Proc. Natl. Acad. Sci. U.S.A 91, 8378-8382 (1994); Liu, K. et al. Characterization of Abeta11-40/42 peptide deposition in Alzheimer's disease and young Down's syndrome brains: implication of N-terminally truncated Abeta species in the pathogenesis of Alzheimer's disease. Acta Neuropathol. 112, 163-174 (2006)). In particular Aβ N3(pE)-42 has been shown to be a major constituent of Aβ deposits in sporadic and familial Alzheimer's disease (FAD) (Saido, T. C. et al. Dominant and differential deposition of distinct beta-amyloid peptide species, A beta N3(pE), in senile plaques. Neuron 14, 457-466 (1995); Miravalle, L. et al. Aminoterminally truncated Abeta peptide species are the main component of cotton wool plaques. Biochemistry 44, 10810-10821 (2005)).

The Aβ N3pE-42 peptides coexist with Aβ 1-40/1-42 peptides (Saido, T. C. et al. Dominant and differential deposition of distinct beta-amyloid peptide species, Abeta N3pE, in senile plaques. Neuron 14, 457-466 (1995); Saido, T. C., Yamao, H., Iwatsubo, T. & Kawashima, S. Amino- and carboxyl-terminal heterogeneity of beta-amyloid peptides deposited in human brain. Neurosci. Lett. 215, 173-176 (1996)), and, based on a number of observations, could play a prominent role in the pathogenesis of AD. For example, a particular neurotoxicity of Aβ N3pE-42 peptides has been outlined (Russo, C. et al. Pyroglutamate-modified amyloid beta-peptides—AbetaN3(pE)—strongly affect cultured neuron and astrocyte survival. J. Neurochem. 82, 1480-1489 (2002) and the pE-modification of N-truncated Aβ peptides confers resistance to degradation by most aminopeptidases as well as Aβ-degrading endopeptidases (Russo, C. et al. Pyroglutamate-modified amyloid beta-peptides—AbetaN3 (pE)—strongly affect cultured neuron and astrocyte survival. J. Neurochem. 82, 1480-1489 (2002); Saido, T. C. Alzheimer's disease as proteolytic disorders: anabolism and catabolism of beta-amyloid. Neurobiol. Aging 19, S69-S75 (1998)). The cyclization of glutamic acid into pE leads to a loss of N-terminal charge resulting in accelerated aggregation of Aβ N3pE compared to the unmodified Aβ peptides (He, W. & Barrow, C. J. The Abeta 3-pyroglutamyl and 11-pyroglutamyl peptides found in senile plaque have greater beta-sheet forming and aggregation propensities in vitro than full-length A beta. Biochemistry 38, 10871-10877 (1999); Schilling, S. et al. On the seeding and oligomerization of pGlu-amyloid peptides (in vitro). Biochemistry 45, 12393-12399 (2006)). Thus, reduction of Aβ N3pE-42 formation should destabilize the peptides by making them more accessible to degradation and would, in turn, prevent the formation of higher molecular weight Aβ aggregates and enhance neuronal survival.

However, for a long time it was not known how the pE-modification of Aβ peptides occurs. Recently, it was discovered that glutaminyl cyclase (QC) is capable to catalyze Aβ N3pE-42 formation under mildly acidic conditions and that specific QC inhibitors prevent Aβ N3pE-42 generation in vitro (Schilling, S., Hoffmann, T., Manhart, S., Hoffmann, M. & Demuth, H.-U. Glutaminyl cyclases unfold glutamyl cyclase activity under mild acid conditions. FEBS Lett. 563, 191-196 (2004); Cynis, H. et al. Inhibition of glutaminyl cyclase alters pyroglutamate formation in mammalian cells. Biochim. Biophys. Acta 1764, 1618-1625 (2006)).

Lewy body dementia (LBD) is a neurodegenerative disorder that can occur in persons older than 65 years of age, and typically causes symptoms of cognitive (thinking) impairment and abnormal behavioral changes. Symptoms can include cognitive impairment, neurological signs, sleep disorder, and autonomic failure. Cognitive impairment is the presenting feature of LBD in most cases. Patients have recurrent episodes of confusion that progressively worsen. The fluctuation in cognitive ability is often associated with shifting degrees of attention and alertness. Cognitive impairment and fluctuations of thinking may vary over minutes, hours, or days. Lewy bodies are formed from phosphorylated and nonphosphorylated neurofilament proteins; they contain the synaptic protein alpha-synuclein as well as ubiquitin, which is involved in the elimination of damaged or abnormal proteins. In addition to Lewy Bodies, Lewy neurites, which are inclusion bodies in the cell processes of the nerve cells, may also be present. Amyloid plaques may form in the brains of patients afflicted with DLB, however they tend to be fewer in number than seen in patients with Alzheimer's disease. Neurofibrillary tangles, the other micropathological hallmark of AD, are not a main characteristic of LBD but are frequently present in addition to amyloid plaques.

Amyotrophic lateral sclerosis (ALS) is characterized by degeneration of upper and lower motor neurons. In some ALS patients, dementia or aphasia may be present (ALS-D). The dementia is most commonly a frontotemporal dementia (FTD), and many of these cases have ubiquitin-positive, tau-negative inclusions in neurons of the dentate gyrus and superficial layers of the frontal and temporal lobes.

Inclusion-body myositis (IBM) is a crippling disease usually found in people over age 50, in which muscle fibers develop inflammation and begin to atrophy—but in which the brain is spared and patients retain their full intellect. Two enzymes involved in the production of amyloid-β protein were found to be increased inside the muscle cells of patients with this most common, progressive muscle disease of older people, in which amyloid-β is also increased.

Another disease that is based on or associated with the accumulation and deposit of amyloid-like protein is macular degeneration. Macular degeneration is a common eye disease that causes deterioration of the macula, which is the central area of the retina (the paper-thin tissue at the back of the eye where light-sensitive cells send visual signals to the brain). Sharp, clear, "straight ahead" vision is processed by the macula. Damage to the macula results in the development of blind spots and blurred or distorted vision. Age-related macular degeneration (AMD) is a major cause of visual impairment in the United States and for people over age 65 it is the leading cause of legal blindness among Caucasians. Approximately 1.8 million Americans of age 40 and older have advanced AMD, and another 7.3 million people with intermediate AMD are at substantial risk for vision loss. The government estimates that by 2020 there will be 2.9 million people with advanced AMD. Victims of AMD are often surprised and frustrated to find out how little is known about the causes and treatment of this blinding condition.

There are two forms of macular degeneration: dry macular degeneration and wet macular degeneration. The dry form, in which the cells of the macula slowly begin to break down, is diagnosed in 85 percent of macular degeneration cases. Both eyes are usually affected by dry AMD, although one eye can lose vision while the other eye remains unaffected. Drusen, which are yellow deposits under the retina, are common early signs of dry AMD. The risk of developing advanced dry AMD or wet AMD increases as the number or size of the drusen increases. It is possible for dry AMD to advance and cause loss of vision without turning into the wet form of the disease; however, it is also possible for early-stage dry AMD to suddenly change into the wet form.

The wet form, although it only accounts for 15 percent of the cases, results in 90 percent of the blindness, and is considered advanced AMD (there is no early or intermediate stage of wet AMD). Wet AMD is always preceded by the dry form of the disease. As the dry form worsens, some people begin to have abnormal blood vessels growing behind the macula. These vessels are very fragile and will leak fluid and blood (hence 'wet' macular degeneration), causing rapid damage to the macula.

The dry form of AMD will initially often cause slightly blurred vision. The center of vision in particular may then become blurred and this region grows larger as the disease progresses. No symptoms may be noticed if only one eye is affected. In wet AMD, straight lines may appear wavy and central vision loss can occur rapidly.

Diagnosis of macular degeneration typically involves a dilated eye exam, visual acuity test, and a viewing of the back of the eye using a procedure called fundoscopy to help diagnose AMD, and—if wet AMD is suspected—fluorescein angiography may also be performed. If dry AMD reaches the advanced stages, there is no current treatment to prevent vision loss. However, a specific high dose formula of antioxidants and zinc may delay or prevent intermediate AMD from progressing to the advanced stage. Macugen® (pegaptanib sodium injection), laser photocoagulation and photodynamic therapy can control the abnormal blood vessel growth and bleeding in the macula, which is helpful for some people who have wet AMD; however, vision that is already lost will not be restored by these techniques. If vision is already lost, low vision aids exist that can help improve the quality of life.

One of the earliest signs of age-related macular degeneration (AMD) is the accumulation of extracellular deposits known as drusen between the basal lamina of the retinal pigmented epithelium (RPE) and Bruch's membrane (BM). Recent studies conducted by Anderson et al. have confirmed that drusen contain amyloid beta. (Experimental Eye Research 78 (2004) 243-256).

The aim of the present invention is to establish a highly sensitive and concomitantly robust detection technique that allows quantitative determination of Aβ variants, in particular pGlu-Aβ peptides, in biological samples, e.g. liquor or serum samples, preferably serum samples. This is a tremendous challenge, taking the low abundance of Aβ peptides in blood into account. Having such a detection technique available is, however, a prerequisite for studying efficacy of small molecule inhibitors in drug screening programs.

The present invention provides novel methods and compositions comprising highly specific and highly effective antibodies, including chimeric antibodies and fragments thereof, including partially or fully humanized antibodies and fragments thereof, having the ability to specifically recognize and bind to specific epitopes from a range of β-amyloid antigens, in particular pGlu-Aβ peptides, which may be presented to the antibody in a monomeric, dimeric, trimeric, etc, or a polymeric form, in form of an aggregate, fibers, filaments or in the condensed form of a plaque. The antibodies enabled by the teaching of the present invention are particularly useful for diagnosis of amyloidosis, a group of diseases and disorders associated with amyloid plaque formation including secondary amyloidosis and age-related amyloidosis including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, hereditary cerebral hemorrhage with amyloidosis Dutch type, Parkinson's disease, HIV-related dementia, ALS (amyotropic lateral sclerosis), Adult Onset Diabetes; senile cardiac amyloidosis; endocrine tumors, and others, including macular degeneration, to name just a few.

To meet all demands mentioned above, an ELISA based technique would be especially preferable. The task was started with Aβ N3pE ELISA, because for this Aβ variant an ELISA system is already commercially available (Human Amyloid β (N3pE) Assay Kit-IBL, Code No. 27716), which is to be used as reference and internal quality control. Capturing of the Aβ N3pE-40 peptide was done with the hAβ (x-40) ELISA (HS) from TGC (The Genetics Company, Inc., Wagistrasse 23, 8952 Schlieren, Zurich area Switzerland), which should facilitate and expedite the process of development.

SUMMARY OF THE INVENTION

The present invention pertains in particular to antibodies or variants thereof, which are characterized in that they bind to Aβ-peptide with a high affinity. Said high affinity means in the context of the present invention an affinity of a $K_D$ value of $10^{-7}$ M or better, preferably a $K_D$ value of $10^{-8}$ M or better, and even more preferably a $K_D$ value of $10^{-9}$ M–$10^{-12}$ M.

In particular the antibody is preferably a monoclonal antibody and is selected from the following group

Aβ 5-5-6
Aβ 6-1-6
Aβ 17-4-3
Aβ 24-2-3

The antibody according to the present invention is especially useful in a diagnostic method to detect amyloidosis, in particular Alzheimer's disease.

Other objects and features will be in part apparent and in part pointed out hereinafter.

DESCRIPTION OF THE FIGURES

Those of skill in the art will understand that the drawings, described below, are for illustrative purposes only. The drawings are not intended to limit the scope of the present teachings in any way.

Detection of 10 ng/ml amyloid β N3pE-40 by increasing concentrations of pGlu-6166 antibody (clone 12-1).

FIG. 1B

Determination of the highest concentration of pGlu-6166 antibody (clone 12-1) required for detection of 10 ng/ml amyloid β N3pE-40.

FIG. 2

Dot Blot analysis of hybridoma cell culture supernatants of individual IgG producing clones.

FIG. 3

PepSpot Analysis of pGlu-6166 Hybridoma Cell Clones and IBL-Aβ N3pE antibody.

FIG. 4

12% SDS-PAGE of 20 μg pGlu-6166 antibody and hybridoma cell culture supernatants.

FIG. 5

Biacore analysis of hybridoma cell culture supernatants. An overlay of monitored binding courses is illustrated graphically.

FIG. 6

Sensograms of interaction of anti-AβN3pE antibody clone 6-1-6 with AβpE3-40.

FIG. 7

Sensograms of interaction of anti-AβN3pE antibody clone 24-2-3 with AβpE3-40.

FIG. 8

N3pE-ELISA for clone 6-1-6, standard curve of AβpE3-40.

FIG. 9:

Sensograms of N3pE antibody clone 6-1-6.

FIG. 10

Quantification of AβpE3-42 using the method of neutralization by 1:20 dilution in EIA buffer, pH titration with 860 μl 3.5 M Tris.

FIG. 11A-FIG. 11C

Figure 11A:
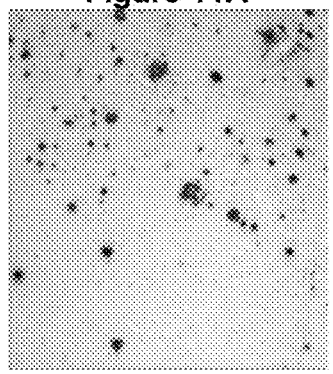
Figure 11B:
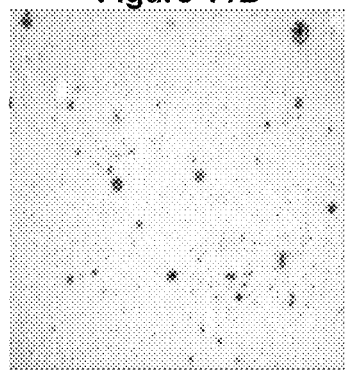
Figure 11C:
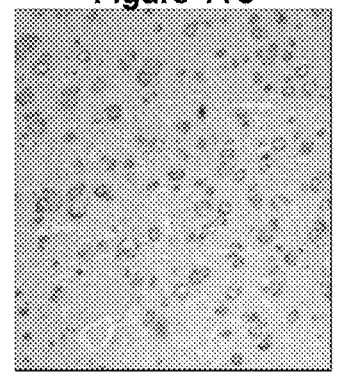

Stained brain sections form Alzheimer's disease (AD) patients (FIG. 11A) Brain of a sporadic AD (SAD) patient stained with anti-Aβ antibody 6E10, recognizing total Aβ, (FIG. 11B) Brain of a sporadic AD (SAD) patient stained with N3pE antibody clone 24-2-3, recognizing AβpE3-x, (FIG. 11C) Brain of a familial AD (FAD) patient stained with N3pE antibody clone 24-2-3, recognizing AβpE3-x.

DETAILED DESCRIPTION OF THE PRESENTLY PREFERRED EMBODIMENTS

Definitions

The following definitions and methods are provided to better define the present invention and to guide those of ordinary skill in the art in the practice of the present invention. Unless otherwise noted, terms are to be understood according to conventional usage by those of ordinary skill in the relevant art.

The term "antibody" is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. The antibody may be an IgM, IgG (e.g. $IgG_1$, IgG2, IgG3 or IgG4), IgD, IgA or IgE, for example. Preferably however, the antibody is not an IgM antibody.

"Antibody fragments" comprise a portion of an intact antibody, generally the antigen binding or variable region of the intact antibody. Examples of antibody fragments include Fab, Fab', F(ab')2, and Fv fragments: diabodies; single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to "polyclonal antibody" preparations which typically include different antibodies directed against different determinants (epitopes), each monoclonal antibody is directed against a single determinant on the antigen. In addition to their specificity, the monoclonal antibodies can frequently be advantageous in that they are synthesized by the hybridoma culture, uncontaminated by other immunoglobulins. The "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Köhler et al., Nature, 256:495 (1975), or may be made by generally well known recombinant DNA methods. The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein specifically include chimeric antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain a minimal sequence derived from a non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321:522-525 (1986), Reichmann et al, Nature. 332:323-329 (1988): and Presta, Curr. Op. Struct. Biel., 2:593-596 (1992). The humanized antibody includes a Primatized™ antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_D$) in the same polypeptide chain ($V_H$-$V_D$). By using a linker that is too short to allow pairing between the two domains on the same chain, the domains are forced to pair with the complementary domains of another chain and create two antigen-binding sites. Diabodies are described more fully in Hollinger et al., Proc. Natl. Acad. Sol. USA, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the expressions "cell", "cell line," and "cell culture" are used interchangeably and all such designations include progeny. Thus, the words "transformants" and "transformed cells" include the primary subject cell and culture derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, this will be clear from the context.

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

The language "diseases and disorders which are caused by or associated with amyloid or amyloid-like proteins" includes, but is not limited to, diseases and disorders caused by the presence or activity of amyloid-like proteins in monomeric, fibril, or polymeric state, or any combination of the three. Such diseases and disorders include, but are not limited to, amyloidosis, endocrine tumors, and macular degeneration.

The term "amyloidosis" refers to a group of diseases and disorders associated with amyloid plaque formation including, but not limited to, secondary amyloidosis and age-related amyloidosis such as diseases including, but not limited to, neurological disorders such as Alzheimer's Disease (AD), including diseases or conditions characterized by a loss of cognitive memory capacity such as, for example, mild cognitive impairment (MCI), sporadic Alzheimer's disease, Lewy body dementia, Down's syndrome, hereditary cerebral hemorrhage with amyloidosis (Dutch type); the Guam Parkinson-Dementia complex, familial forms of Alzheimer's disease like Familial British Dementia (FBD) and Familial Danish Dementia (FDD); as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), inclusion-body myositis (IBM), Adult Onset Diabetes, and senile cardiac amyloidosis; and various eye diseases including macular degeneration, drusen-related optic neuropathy, and cataract due to beta-amyloid deposition.

"Amyloid β, Aβ or/β-amyloid" is an art recognized term and refers to amyloid β proteins and peptides, amyloid β precursor protein (APP), as well as modifications, fragments and any functional equivalents thereof. In particular, by amyloid β as used herein is meant any fragment produced by proteolytic cleavage of APP but especially those fragments which are involved in or associated with the amyloid pathologies including, but not limited to, $Aβ_{1-38}$, $Aβ_{1-40}$, $Aβ_{1-42}$. The amino acid sequences of these Aβ peptides are as follows:

Aβ 1-42 (SEQ ID NO. 1):
Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly-Val-Val-Ile-Ala

Aβ 1-40 (SEQ ID NO. 2):
Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly-Val-Val

```
Aβ 1-38 (SEQ ID NO. 3):
Asp-Ala-Glu-Phe-Arg-His-Asp-Ser-Gly-Tyr-Glu-Val-

His-His-Gln-Lys-Leu-Val-Phe-Phe-Ala-Glu-Asp-Val-

Gly-Ser-Asn-Lys-Gly-Ala-Ile-Ile-Gly-Leu-Met-Val-

Gly-Gly
```

"pGlu-Aβ" or "Aβ N3pE" refers to N-terminally truncated forms of Aβ, that start at the glutamic acid residue at position 3 in the amino acid sequence of Aβ, and wherein said glutamic acid residue is cyclized to form a pyroglutamic acid residue. In particular, by pGlu-Aβ as used herein are meant those fragments which are involved in or associated with the amyloid pathologies including, but not limited to, pGlu-Aβ$_{3-38}$, pGlu-Aβ$_{3-40}$, p-Glu-Aβ$_{3-42}$.

The sequences of the N-terminally truncated forms of Aβ, Aβ$_{3-38}$, Aβ$_{43-40}$, Aβ$_{43-42}$ are as follows:

```
Aβ 3-42 (SEQ ID NO. 4):
Glu-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly-

Val-Val-Ile-Ala

Aβ 3-40 (SEQ ID NO. 5):
Glu-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly-

Val-Val

Aβ 3-38 (SEQ ID NO. 6):
Glu-Phe-Arg-His-Asp-Ser-Gly-Tyr-Glu-Val-His-His-

Gln-Lys-Leu-Val-Phe-Phe-Ala-Glu-Asp-Val-Gly-Ser-

Asn-Lys-Gly-Ala-Ile-Ile-Gly-Leu-Met-Val-Gly-Gly
```

In particular the present invention pertains to the following items:

1. Antibody, characterised in that it binds to Aβ peptides or variants thereof, preferably with high affinity.
2. Antibody according to item 1, wherein said high affinity means a dissociation constant ($K_D$) value of $10^{-7}$ M, or better.
3. Antibody according to item 1 or 2, wherein said antibody is a monoclonal antibody.
4. Antibody according to any of the preceding items, wherein the variable part of the light chain of said antibody has a nucleotide sequence selected from SEQ ID NOs: 49, 53, 57 and 61, or having an amino acid sequence selected from SEQ ID NOs: 50, 54, 58, and 62.
5. Antibody according to any of the preceding items, wherein the variable part of the heavy chain of said antibody has a nucleotide sequence selected from SEQ ID NOs: 51, 55, 59 and 63, or having an amino acid sequence selected from SEQ ID NOs: 52, 56, 60 and 64.
6. Antibody according to any of the preceding items, wherein the variable part of the light chain of said antibody has the nucleotide sequence of SEQ ID NO: 49 or the amino acid sequence of SEQ ID NO: 50, and wherein the variable part of the heavy chain of said antibody has the nucleotide sequence of SEQ ID NO: 51, or the amino acid sequence of SEQ ID NO: 52.
7. Antibody according to any of the preceding items, wherein the variable part of the light chain of said antibody has the nucleotide sequence of SEQ ID NO: 53 or the amino acid sequence of SEQ ID NO: 54, and wherein the variable part of the heavy chain of said antibody has the nucleotide sequence of SEQ ID NO: 55, or the amino acid sequence of SEQ ID NO: 56.
8. Antibody according to any of the preceding items, wherein the variable part of the light chain of said antibody has the nucleotide sequence of SEQ ID NO: 57 or the amino acid sequence of SEQ ID NO: 58, and wherein the variable part of the heavy chain of said antibody has the nucleotide sequence of SEQ ID NO: 59, or the amino acid sequence of SEQ ID NO: 60.
9. Antibody according to any of the preceding items, wherein the variable part of the light chain of said antibody has the nucleotide sequence of SEQ ID NO: 61 or the amino acid sequence of SEQ ID NO: 62, and wherein the variable part of the heavy chain of said antibody has the nucleotide sequence of SEQ ID NO: 63, or the amino acid sequence of SEQ ID NO: 64.
10. Antibody according to any of the preceding items, wherein said antibody is selected from the following group:
    Aβ 5-5-6 (Deposit No. DSM ACC 2923)
    Aβ 6-1-6 (Deposit No. DSM ACC 2924)
    Aβ 17-4-3 (Deposit No. DSM ACC 2925)
    Aβ 24-2-3 (Deposit No. DSM ACC 2926)
    or functional variants thereof.
11. Antibody according to any of the preceding items, wherein said antibody is Aβ 6-1-6 (Deposit No. DSM ACC 2924).
12. Antibody according to any of the preceding items, wherein said antibody is Aβ 24-2-3 (Deposit No. DSM ACC 2926).
13. Antibody according to any of the preceding items, wherein said antibody is a humanized or chimeric antibody, or an antibody fragment which retains the high affinity.
14. Antibody according to any of the preceding items for use in the detection of Aβ peptide or variants thereof.
15. Antibody according to item 14, wherein said variants are selected from the following group:
    pGlu-Aβ$_{3-38}$
    pGlu-Aβ$_{3-40}$
    pGlu-Aβ$_{3-42}$, and
    pGlu-Aβ$_{3-x}$ variants,
    wherein x is an integer between 10 and 42; preferably 18 and 42, more preferably 30 and 42.
16. Antibody according to any of the preceding items, which is human.
17. Antibody according to any of the preceding items, which is a diabody or a single chain antibody which retains the high affinity.
18. Antibody according to any of the preceding items, which binds to the epitope bound by the antibodies defined in item 15.
19. Antibody according to any of the preceding items, which has the complementarity determining regions of the antibodies as defined in item 15.
20. Antibody according to any of the preceding items, which is labeled.
21. Antibody according to any of the preceding items, which is immobilised on a solid phase.
22. Antibody obtainable from any one of hybridoma cell lines DSM ACC 2923, DSM ACC 2924, DSM ACC 2925, DSM ACC 2926.

23. Composition comprising the antibody as defined in any of the preceding items.
24. Composition according to item 23 for the treatment, prevention or delay of amyloidosis.
25. Composition according to item 23 or 24, wherein said amyloidosis is a neurodegenerative disease selected from the group consisting of mild cognitive impairment, Alzheimer's disease and neurodegeneration in Down Syndrome.
26. Composition according to item 23 or 24, wherein said amyloidosis is sporadic Alzheimer's disease or a Familial Alzheimer's dementia.
27. Composition according to item 26, wherein said Familial Alzheimer's dementia is Familial British Dementia or Familial Danish Dementia.
28. Hybridoma cell line DSM ACC 2923.
29. Hybridoma cell line DSM ACC 2924
30. Hybridoma cell line DSM ACC 2925.
31. Hybridoma cell line DSM ACC 2926.
32. Use of the antibody as defined in any one of items 1 to 22 or the composition as defined in any one of items 23 to 27 in a diagnostic or therapeutic method.
33. The use according to item 32 for the diagnosis of an amyloid-associated disease or condition.
34. The use according to item 33, wherein said amyloidosis is a neurodegenerative disease selected from the group consisting of mild cognitive impairment, Alzheimer's disease and neurodegeneration in Down Syndrome.
35. The use according to item 33, wherein said amyloidosis is sporadic Alzheimer's disease or a Familial Alzheimer's dementia.
36. The use according to item 35, wherein said Familial Alzheimer's dementia is Familial British Dementia or Familial Danish Dementia.
37. In vitro diagnostic method for the diagnosis of an amyloid-associated disease or condition, in particular Alzheimer's disease, comprising the following steps:
    contacting an antibody according to any one of items 1 to 22 with a sample from a subject suspected to be afflicted with said disease or condition, and
    detecting binding of the antibody to a pGlu-amyloid protein, preferably pGlu-Aβ peptide from the sample.
38. Diagnostic kit, comprising the antibody as defined in any one of items 1 to 22, and instructions for use, and—optionally—(a) further biologically active substance(s).
39. The diagnostic kit of item 32, wherein said further biological substance is an inhibitor of glutaminy cyclase.
40. An oligonucleotide selected from the group consisting of SEQ ID Nos: 23 to 48.

The antibodies of the invention may be useful for the diagnosis of amyloidosis.

The antibodies of the invention may be used as affinity purification agents. In this process, the antibodies are immobilised on a solid phase such a Sephadex resin or filter paper, using methods well known in the art. The immobilized antibody is contacted with a sample containing the Aβ-peptide (or fragment thereof) to be purified, and thereafter the support is washed with a suitable solvent that will remove substantially all the material in the sample except the Aβ-peptide, which is bound to the immobilized antibody. Finally, the support is washed with another suitable solvent, such as glycine buffer, pH 5.0 that will release the Aβ-peptide from the antibody.

Anti-Aβ-peptide antibodies may also be useful in diagnostic assays for Aβ-peptide, e.g. detecting its occurrence in specific cells, tissues, or serum. Thus, the antibodies may be used in the diagnosis of amyloidosis, in particular a neurodegenerative disease selected from the group consisting of mild cognitive impairment (MCI), Alzheimer's disease (AD), like for instance sporadic Alzheimer's disease (SAD) or Familial Alzheimer's dementias (FAD) such as Familial British Dementia (FBD) and Familial Danish Dementia (FDD) and neurodegeneration in Down Syndrome; preferably Alzheimer's disease.

For diagnostic applications, the antibody typically will be labelled with a detectable moiety. Numerous labels are available which can be generally grouped into the following categories:

(a) Radioisotopes, such as $^{35}S$, $^{14}C$, $^{125}I$, $^{3}H$, and $^{131}I$. The antibody can be labeled with the radioisotope using the techniques described in Current Protocols in Immunology, Volumes 1 and 2, Gütigen et al., Ed., Wiley-Interscience. New York, N.Y. Pubs., (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in Current Protocols in Immunology, supra for example. Fluorescence can be quantified using a fluorimeter.

(c) Various enzyme-substrate labels are available. The enzyme generally catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase. 0-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym (ed Langone & H. Van Vunakis), Academic Press, New York, 73: 147-166 (1981).

Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine (OPD) or 3,3',5,5'-tetramethyl benzidine hydrochloride (TMB));

(ii) alkaline phosphatase (Aβ) with para-Nitrophenyl phosphate as chromogenic substrate; and (iii) β-D-galactosidase (β-D-Gal) with a chromogenic substrate (e.g. p-nitrophenyl-β-D-galactosidase) or the fluorogenic substrate 4-methylumbelliferyl-β-D-galactosidase.

Numerous other enzyme-substrate combinations are available to those skilled in the art.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

The Aβ-antibody needs not be labeled, and the presence thereof can be detected using a labeled antibody, which binds to the Aβ-antibody.

The antibodies of the present invention may be employed in any known assay method, such as competitive binding assays, direct and indirect sandwich assays, and immunoprecipitation assays. Zola, *Monoclonal Antibodies A Manual of Techniques*, pp. 147-158 (CRC Press. Inc., 1987)

Competitive binding assays rely on the ability of a labeled standard to compete with the test sample analyte for binding with a limited amount of antibody. The amount of Aβ peptide in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. The second antibody may itself be labeled with a detectable moiety (direct sandwich assays) or may be measured using an anti-immunoglobulin antibody that is labeled with a detectable moiety (indirect sandwich assay). For example, one preferable type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

Diagnostic Kits

As a matter of convenience, the antibody of the present invention can be provided in a kit, i.e., a packaged combination of reagents in predetermined amounts with instructions for performing the diagnostic assay. Where the antibody is labelled with an enzyme, the kit will include substrates and cofactors required by the enzyme (e.g. a substrate precursor which provides the detectable chromophore or fluorophore). In addition, other additives may be included such as stabilizers, buffers (e.g. a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

The diagnostic kit according to the invention may contain a further biologically active substance as described below. Especially preferred for the use in the diagnostic kit are inhibitors of glutaminyl cyclase.

The diagnostic kit of the invention is especially useful for the detection and diagnosis of amyloid-associated diseases and conditions, in particular neurodegenerative diseases selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease.

The present invention pertains in particular to antibodies which are characterized in that they bind to Aβ-peptide with a high affinity. The present invention also pertains to antibodies which are characterised in that they bind to Aβ-peptides or variants thereof with a high affinity. Said high affinity means in the context of the present invention an affinity of a $K_D$ value of $10^{-7}$ M or better, preferably a $K_D$ value of $10^{-8}$ M or better, and even more preferably a $K_D$ value of $10^{-9}$ M–$10^{-12}$ M. Thereby, the inventive antibodies bind to Aβ-peptide with a higher affinity than previously known antibodies.

In particular the antibody is preferably a monoclonal antibody and is selected from the following group Aβ 5-5-6 (DSM ACC 2923)
Aβ 6-1-6 (DSM ACC 2924)
Aβ 17-4-3 (DSM ACC 2925)
Aβ 24-2-3 (DSM ACC 2926)

The antibody according to the present invention is especially useful in a diagnostic method to detect amyloidosis, in particular a neurodegenerative disease selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease.

According to a preferred embodiment, the antibody can be humanised or is a chimeric antibody or is a human antibody.

Further, the antibody as selected from the above-mentioned group can also be a functional variant of said group.

In the context of the present invention, a variant of an p-Glu-Aβ peptide is in particular pGlu-Aβ$_{3-38}$,
pGlu-Aβ$_{3-40}$,
pGlu-Aβ$_{3-42}$ Further variants of Aβ peptides are all pGlu-Aβ$_{3-x}$ variants, which have been shown to accumulate in the brain as a consequence of Alzheimer's disease or preceding Alzheimer's disease. X is defined as an integer between 10 and 42, e.g. in the above pGlu-Aβ$_{3-42}$, "42" would be the integer for "x".

In the context of the present invention a "functional variant" of the inventive antibody is an antibody which retains the binding capacities, in particular binding capacities with high affinity to a pGlu-Aβ$_{3-x}$ peptide or functional variant thereof. The provision of such functional variants is known in the art and encompasses the above-mentioned possibilities, which were indicated under the definition of antibodies and fragments thereof.

In a preferred embodiment, the antibody is an antibody fragment, as defined above.

In a further preferred embodiment, the inventive antibody is an antibody which binds to the epitope which is bound by the antibodies as defined above, in particular antibody 5-5-6, antibody 6-1-6, antibody 17-4-3 and antibody 24-2-3.

In a further preferred embodiment, the antibody of the invention is an antibody which has the complementarity-determining regions (CDRs) of the above-defined antibodies. Preferably, the antibody can be labeled; possible labels are those as mentioned above and all those known to a person skilled in the art of diagnostic uses of antibodies in particular.

Preferably, the antibody is immobilized on a solid phase.

The present invention also concerns an antibody which is obtainable from hybridoma cell line 6-1-6 (DSM ACC 2924).

The present invention also relates to a composition which comprises the antibody as defined above. In particular, said composition is a composition for a diagnostic use, especially for the diagnosis of a neurodegenerative disease selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease; in particular by detection of Aβ peptide or variants thereof in a biological sample.

In another embodiment, the antibody according to the invention and as described herein before or a fragment thereof, exhibits an binding affinity to an Aβ oligomer, fiber, fibril or filament which is at least 2 times, particularly at least 4 times, particularly at least 10 times, particularly at least 15 times, more particularly at least 20 times, but especially at least 25 times higher than the binding affinity to an Aβ monomer.

In still another embodiment, an antibody or a fragment thereof or a chimeric antibody or a fragment thereof, or a humanized antibody or a fragment thereof is provided as described herein before, which antibody substantially binds to aggregated Aβ, including Aβ plaques, in the mammalian, particularly the human brain but, preferably, does not show any significant cross-reactivity with amyloid precursor protein (APP).

In another aspect of the invention, the antibody or a fragment thereof or the chimeric antibody or a fragment thereof, or a humanized antibody or a fragment thereof is provided as described herein before, which antibody substantially binds to soluble polymeric amyloid, particularly amyloid β (Aβ), including Aβ monomers, in the mammalian, particularly the human brain but, preferably, does not show any significant cross-reactivity with amyloid precursor protein (APP).

The present invention relates also to humanized forms of the antibodies as defined above, compositions comprising said humanized antibodies and the use of said compositions for the treatment of amyloidosis, especially for the treatment of neurodegenerative disease in a mammal, in particular in a human. Said neurodegenerative disease is in particular selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome. Preferably, said neurodegenerative disease is Alzheimer's disease.

The present invention is also directed to the following hybridoma cell lines 5-5-6, 6-1-6, 17-4-3 and 24-2-3.

The present invention also pertains to the use of the antibody or the composition comprising the antibody, both as defined above, for use in an in vitro diagnostic method. In particular, this diagnostic method is directed to diagnosis of a neurodegenerative disease selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease; especially by detecting an Aβ peptide or variants thereof in a biological sample.

Preferably, said sample is a serum sample.

According to another preferred embodiment, said sample is a liquor or cerebrospinal fluid (CSF) sample.

In a particularly preferred embodiment, the present invention pertains to the following method:

In vitro or in situ diagnostic method for the diagnosis of an amyloid-associated disease or condition, preferably Alzheimer's disease, comprising the following steps:

contacting an antibody according to the invention with a sample, preferably selected from a serum, liquor or CSF sample, most preferably a serum sample; or a specific body part or body area of a subject suspected to be afflicted with said condition or disease, and detecting binding of the antibody to a pGlu-amyloid protein, preferably pGlu-Aβ peptide, from the sample.

More particularly, the invention relates to a method of diagnosis of an amyloid-associated disease or condition, preferably Alzheimer's disease, comprising detecting the immunospecific binding of an antibody or an active fragment thereof to a pGlu-amyloid protein, preferably pGlu-Aβ peptide, in a sample or in situ which includes the steps of (a) bringing the sample or a specific body part or body area suspected to contain the amyloid protein into contact with an antibody, particularly a monoclonal antibody according to the invention, or a chimeric antibody or a fragment thereof, or a humanized antibody or a fragment thereof according to the invention and as described herein before, and/or a functional part thereof, which antibody binds a pGlu-Aβ peptide;

(b) allowing the antibody and/or a functional part thereof, to bind to the pGlu-Aβ peptide to form an immunological complex;

(c) detecting the formation of the immunological complex; and (d) correlating the presence or absence of the immunological complex with the presence or absence of pGlu-Aβ peptide in the sample or specific body part or area.

Also comprised is a method of determining the extent of amyloidogenic plaque burden in a tissue and/or body fluids comprising (a) obtaining a sample representative of the tissue and/or body fluids under investigation;

(b) testing said sample for the presence of amyloid protein with an antibody, particularly a monoclonal antibody according to the invention, or a chimeric antibody or a fragment thereof, or a humanized antibody or a fragment thereof according to the invention and as described herein before, and/or a functional part thereof;

(c) determining the amount of antibody bound to the protein; and (d) calculating the plaque burden in the tissue and/or body fluids.

In particular, the invention relates to a method of determining the extent of amyloidogenic plaque burden in a tissue and/or body fluids, wherein the formation of the immunological complex in step c) is determined such that presence or absence of the immunological complex correlates with presence or absence of amyloid protein, in particular pGlu-Aβ peptides.

In still another embodiment, the invention relates to a composition comprising the antibody according to the invention, or a chimeric antibody or a fragment thereof, or a humanized antibody or a fragment thereof according to the invention and as described herein before including any functionally equivalent antibody or any derivative or functional parts thereof, in a therapeutically effective amount, in particular a composition which is a pharmaceutical composition optionally further comprising a pharmaceutically acceptable carrier.

In another embodiment of the invention, said composition comprises the antibody in a therapeutically effective amount. Further comprised by the invention is a mixture comprising an antibody, particularly a monoclonal antibody according to the invention, or a chimeric antibody or a fragment thereof, or a humanized antibody or a fragment thereof according to the invention and as described herein before including any functionally equivalent antibody or any derivative or functional parts thereof, in a therapeutically effective amount and, optionally, a further biologically active substance and/or a pharmaceutically acceptable carrier and/or a diluent and/or an excipient.

In particular, the invention relates to a mixture, wherein the further biologically active substance is a compound used in the medication of amyloidosis, a group of diseases and disorders associated with amyloid or amyloid-like protein such as the Aβ protein involved in neurodegenerative diseases selected from the group consisting of mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; preferably Alzheimer's disease.

In another embodiment of the invention, the other biologically active substance or compound may also be a therapeutic agent that may be used in the treatment of amyloidosis caused by amyloid β or may be used in the medication of other neurological disorders.

The other biologically active substance or compound may exert its biological effect by the same or a similar mechanism as the antibody according to the invention or by an unrelated mechanism of action or by a multiplicity of related and/or unrelated mechanisms of action.

Generally, the other biologically active compound may include neutron-transmission enhancers, psychotherapeutic drugs, acetylcholine esterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists. More particularly, the invention relates to a mixture comprising at least one compound selected from the group consisting of compounds effective against oxidative stress, anti-apoptotic compounds, metal chelators, inhibitors of DNA repair such as pirenzepin and metabolites, 3-amino-1-propanesulfonic acid (3 APS), 1,3-propanedisulfonate (1,3PDS), α-secretase activators, β- and γ-secretase inhibitors, tau proteins, neurotransmitter, /3-sheet breakers, attractants for amyloid beta clearing/depleting cellular components, inhibitors of N-terminal truncated amyloid beta including pyroglutamated amyloid beta 3-42, such as inhibitors of glutaminyl cyclase, anti-inflammatory molecules, or cholinesterase inhibitors (ChEIs) such as tacrine, rivastigmine, donepezil, and/or galantamine, M1 agonists and other drugs including any amyloid or tau modifying drug and nutritive supplements, and nutritive supplements, together with an antibody according to the present invention and, optionally, a pharmaceutically acceptable carrier and/or a diluent and/or an excipient.

The invention further relates to a mixture, wherein the compound is a cholinesterase inhibitor (ChEIs), particularly a mixture, wherein the compound is one selected from the group consisting of tacrine, rivastigmine, donepezil, galantamine, niacin and memantine.

In a further embodiment, the mixtures according to the invention may comprise niacin or memantine together with an antibody according to the present invention and, optionally, a pharmaceutically acceptable carrier and/or a diluent and/or an excipient.

In a further embodiment, the mixtures according to the invention may comprise a glutaminyl cyclase inhibitor together with an antibody according to the present invention and, optionally, a pharmaceutically acceptable carrier and/or a diluent and/or an excipient.

Preferred inhibitors of glutaminyl cyclase are described in WO 2005/075436, in particular examples 1-141 as shown on pp. 31-40. The synthesis of examples 1-141 is shown on pp. 40-48 of WO 2005/075436. The disclosure of WO 2005/075436 regarding examples 1-141, their synthesis and their use as glutaminyl cyclase inhibitors is incorporated herein by reference.

Further preferred inhibitors of glutaminyl cyclase are described in WO 2008/055945, in particular examples 1-473 as shown on pp. 46-155. The synthesis of examples 1-473 is shown on pp. 156-192 of WO 2008/055945. The disclosure of WO 2008/055945 regarding examples 1-473, their synthesis and their use as glutaminyl cyclase inhibitors is incorporated herein by reference.

Further preferred inhibitors of glutaminyl cyclase are described in WO 2008/055947, in particular examples 1-345 as shown on pp. 53-118. The synthesis of examples 1-345 is shown on pp. 119-133 of WO 2008/055947. The disclosure of WO 2008/055947 regarding examples 1-345, their synthesis and their use as glutaminyl cyclase inhibitors is incorporated herein by reference.

Further preferred inhibitors of glutaminyl cyclase are described in WO 2008/055950, in particular examples 1-212 as shown on pp. 57-120. The synthesis of examples 1-212 is shown on pp. 121-128 of WO 2008/055950. The disclosure of WO 2008/055950 regarding examples 1-212, their synthesis and their use as glutaminyl cyclase inhibitors is incorporated herein by reference.

Further preferred inhibitors of glutaminyl cyclase are described in WO2008/065141, in particular examples 1-25 as shown on pp. 56-59. The synthesis of examples 1-25 is shown on pp. 60-67 of WO2008/065141. The disclosure of WO2008/065141 regarding examples 1-25, their synthesis and their use as glutaminyl cyclase inhibitors is incorporated herein by reference.

Further preferred inhibitors of glutaminyl cyclase are described in WO 2008/110523, in particular examples 1-27 as shown on pp. 55-59. The synthesis of examples 1-27 is shown on pp. 59-71 of WO 2008/110523. The disclosure of WO 2008/110523 regarding examples 1-27, their synthesis and their use as glutaminyl cyclase inhibitors is incorporated herein by reference.

Further preferred inhibitors of glutaminyl cyclase are described in WO 2008/128981, in particular examples 1-18 as shown on pp. 62-65. The synthesis of examples 1-18 is shown on pp. 65-74 of WO 2008/128981. The disclosure of WO 2008/128981 regarding examples 1-18, their synthesis and their use as glutaminyl cyclase inhibitors is incorporated herein by reference.

Further preferred inhibitors of glutaminyl cyclase are described in WO 2008/128982, in particular examples 1-44 as shown on pp. 61-67. The synthesis of examples 1-44 is shown on pp. 68-83 of WO 2008/128982. The disclosure of WO 2008/128982 regarding examples 1-44, their synthesis and their use as glutaminyl cyclase inhibitors is incorporated herein by reference.

Further preferred inhibitors of glutaminyl cyclase are described in WO 2008/128983, in particular examples 1-30 as shown on pp. 64-68. The synthesis of examples 1-30 is shown on pp. 68-80 of WO 2008/128983. The disclosure of WO 2008/128983 regarding examples 1-30, their synthesis and their use as glutaminyl cyclase inhibitors is incorporated herein by reference.

Further preferred inhibitors of glutaminyl cyclase are described in WO 2008/128984, in particular examples 1-36 as shown on pp. 63-69. The synthesis of examples 1-36 is shown on pp. 69-81 of WO 2008/128984. The disclosure of WO 2008/128984 regarding examples 1-36, their synthesis and their use as glutaminyl cyclase inhibitors is incorporated herein by reference.

Further preferred inhibitors of glutaminyl cyclase are described in WO 2008/128985, in particular examples 1-71 as shown on pp. 66-76. The synthesis of examples 1-71 is shown on pp. 76-98 of WO 2008/128985. The disclosure of WO 2008/128985 regarding examples 1-71, their synthesis and their use as glutaminyl cyclase inhibitors is incorporated herein by reference.

Further preferred inhibitors of glutaminyl cyclase are described in WO 2008/128986, in particular examples 1-7 as shown on pp. 65-66. The synthesis of examples 1-7 is shown on pp. 66-73 of WO 2008/128986. The disclosure of WO 2008/128986 regarding examples 1-7, their synthesis and their use as glutaminyl cyclase inhibitors is incorporated herein by reference.

In still another embodiment of the invention mixtures are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with an antibody, particularly a monoclonal antibody according to the invention, but particularly a chimeric antibody or a fragment thereof, or a humanized antibody or a fragment thereof according to the invention and as described herein and, optionally, a pharmaceutically acceptable carrier and/or a diluent and/or an excipient.

In a specific embodiment of the invention, the compositions and mixtures according to the invention and as described herein before comprise the antibody and the biologically active substance, respectively, in a therapeutically effective amount.

Other compounds that can be suitably used in mixtures in combination with the antibody according to the present invention are described in WO2008/065141 (see especially pages 37/38), including PEP-inhibitors (pp. 43/44), LiCl, inhibitors of dipeptidyl aminopeptidases, preferably inhibitors of DP IV or DP IV-like enzymes (see pp. 48/49); acetylcholinesterase (ACE) inhibitors (see p. 47), PIMT enhancers, inhibitors of beta secretases (see p. 41), inhibitors of gamma secretases (see pp. 41/42), inhibitors of neutral endopeptidase, inhibitors of phosphodiesterase-4 (PDE-4) (see pp. 42/43), TNFalpha inhibitors, muscarinic M1 receptor antagonists (see p. 46), NMDA receptor antagonists (see pp. 47/48), sigma-1 receptor inhibitors, histamine H3 antagonists (see p. 43), immunomodulatory agents, immunosuppressive agents or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS; beta-amyloid antibodies (see p. 44), cysteine protease inhibitors (see p. 44); MCP-1 antagonists (see pp. 44/45), amyloid protein deposition inhibitors (see 42) and beta amyloid synthesis inhibitors (see p. 42), which document is incorporated herein by reference.

In another embodiment, the invention relates to a mixture comprising the antibody, particularly a monoclonal antibody according to the invention, or a chimeric antibody or a fragment thereof, or a humanized antibody or a fragment thereof according to the invention and as described herein before and/or the biologically active substance in a therapeutically effective amount.

The invention further relates to the use of an antibody, particularly a monoclonal antibody according to the invention, but particularly a chimeric antibody or a fragment thereof, or a humanized antibody or a fragment thereof according to the invention and as described herein before and/or a functional part thereof and/or a pharmaceutical composition, or a mixture comprising said antibody, for the preparation of a medicament for treating or alleviating the effects of amyloidosis, a group of diseases and disorders associated with amyloid plaque formation including secondary amyloidosis and age-related amyloidosis such as diseases including, but not limited to, neurological disorders such as Alzheimer's Disease (AD), Lewy body dementia, Down's syndrome, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration.

Also comprised by the present invention is a method for the preparation of an antibody, particularly a monoclonal antibody according to the invention, but particularly a chimeric antibody or a fragment thereof, or a humanized antibody or a fragment thereof according to the invention and as described herein before and/or a functional part thereof and/or a pharmaceutical composition, or a mixture comprising said antibody and/or a functional part thereof, particularly in a therapeutically effective amount, for use in a method of preventing, treating or alleviating the effects of amyloidosis, a group of diseases and disorders associated with amyloid plaque formation including secondary amyloidosis and age-related amyloidosis such as diseases including, but not limited toneurodegenerative diseases such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; Lewy body dementia, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration comprising formulating an antibody, particularly a monoclonal antibody according to the invention, but particularly a chimeric antibody or a fragment thereof, or a humanized antibody or a fragment thereof according to the invention in a pharmaceutically acceptable form.

Further comprised by the present invention is a method for preventing, treating or alleviating the effects of amyloidosis, a group of diseases and disorders associated with amyloid plaque formation including secondary amyloidosis and age-related amyloidosis such as diseases including, but not limited to, neurological disorders such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; Lewy body dementia, hereditary cerebral hemorrhage with amyloidosis (Dutch type); the Guam Parkinson-Dementia complex; as well as other diseases which are based on or associated with amyloid-like proteins such as progressive supranuclear palsy, multiple sclerosis; Creutzfeld Jacob disease, Parkinson's disease, HIV-related dementia, ALS (amyotropic lateral sclerosis), Adult Onset Diabetes; senile cardiac amyloidosis; endocrine tumors, and others, including macular degeneration by administering an antibody and/or a functional part thereof, but particularly a humanized antibody and/or a functional part thereof, or a composition or mixture comprising such an antibody and/or a functional part thereof, to an animal or a human affected by such a disorder comprising administering the antibody in a therapeutically effective amount.

It is also an object of the invention to provide a method for the treatment of amyloidosis, a group of diseases and disorders associated with amyloid plaque formation including secondary amyloidosis and age-related amyloidosis including, but not limited to, neurodegenerative diseases such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; particularly a disease or condition characterized by a loss of cognitive memory capacity by administering to an animal, particularly a mammal or a human, an antibody, particularly a pharmaceutical composition according to the invention and as described herein.

In a specific embodiment the invention provides a method for retaining or increasing cognitive memory capacity but, particularly, for restoring the cognitive memory capacity of an animal, particularly a mammal or a human, suffering from memory impairment by administering to an animal, particularly a mammal or a human, an antibody, particularly a pharmaceutical composition according to the invention and as described herein before.

It is a further object of the invention to provide a therapeutic composition and a method of producing such a composition as well as a method for the treatment of amyloidosis, a group of diseases and disorders associated with amyloid plaque formation including secondary amyloidosis and age-related amyloidosis including, but not limited to, neurodegenerative diseases such as mild cognitive impairment (MCI), Alzheimer's disease (AD), like for instance sporadic Alzheimer's disease (SAD) or Familial Alzheimer's dementias (FAD) like Familial British Dementia (FBD) and Familial Danish Dementia (FDD), neurodegeneration in Down Syndrome; particularly a disease or condition characterized by a loss of cognitive memory capacity, using an antibody according to the invention and as described herein before.

In particular, the invention relates to the treatment of an animal, particularly a mammal or a human, suffering from an amyloid-associated condition characterized by a loss of cognitive memory capacity that leads to the retention of cognitive memory capacity.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

1. Material and Methods 1.1 Production of Antibodies

Mice

For the production of hybridomas, female BALB/C mice (Charles River) of 8 weeks age were used.

Myeloma Cell Line

For the generation of the hybridomas, the myeloma cell line SP2/0-Ag14 from Deutsche Stammsammlung von Mikoorganismen and Zellkulturen was used.

Antigen

The peptide pGlu-6166 (sequence pGlu-FRHDSGC, SEQ ID NO: 65) was used.

Strategy

As an immunogen, the peptide was coupled to bovine thyroglubulin (BTG, SIGMA) via maleimid groups from three different linkers. The three linkers of different length were used from N-[e-maleimidocaproyloxy]succinimide ester (EMCS), succiminidyl-4-(N-maleimidomethyl)-cyclohexan-1-carboxy-(6-amidocaproate) (LCSMCC) and N-[b-maleimidopropyloxy]succinimide ester (BMPS). For the detection of the generated antibodies, the same peptide was conjugated to bovine serum albumine (BSA, SIGMA) via maleimid groups from succinimidyl-6-[(b-maleimido-propionamido)hexanoate] (SMPH).

Methods

Conjugation of the Peptide for Immunization

Conjugation was performed in two steps via SH-groups from the cystein residue of the peptide.

1. Maleoylation of the Carrier Protein 2 to 5 mg of the respective linker (50 mg/ml in N-methylpyrrolidone, NMP) was added to 2 ml of the carrier protein solution (10 mg/ml in 0.1 mM NaHCO3, pH 8.0). The reaction mixture was incubated for 1 h at room temperature (RT). The reaction mixture was thereafter desalted using a Sephadex G-50 column (1.5×14 cm), which was equilibrated with 50 mM sodium phosphate, 250 mM NaCl, pH 6.8.

2. Coupling of the Maleoylated BTG with the Peptide

250 µl of the peptide solution (10 mg/ml in Aqua bidest) were mixed with 2 ml of a solution containing the maleoylated carrier proteins (2.5 mg/ml) in 50 mM sodium phosphate, 250 ml NaCl, pH 6.8 and incubated for 2 h at 4° C. and further 4 h at RT. Unreacted maleimid groups were blocked by addition of 2-mercaptoethanole up to a concentration of 10 mM and over night incubation at 4° C. The resulting conjugate was dialysed against 10 mM sodium phosphate, 150 mM NaCl, pH 7.5 at 4° C. (3 times buffer exchange, MW cut-off 10.000).

Conjugation of the Peptide for ELISA

Conjugation was performed in two steps via SH-groups from the cystein residue of the peptide.

1. Maleoylation of the Carrier Protein 2 mg SMPH (50 mg/ml in N-methylpyrrolidone, NMP) was added to 2 ml of the carrier protein solution (BSA, 10 mg/ml in 0.1 mM NaHCO3, pH 8.0). The reaction mixture was incubated for 1 h at room temperature (RT). The reaction mixture was thereafter desalted using a Sephadex G-50 column (1.5×14 cm), which was equilibrated with 50 mM sodium phosphate, 250 mM NaCl, pH 6.8.

2. Coupling of the Maleoylated BTG with the Peptide

100 µl of the peptide solution (10 mg/ml in 50 mM sodium phosphate, 250 mM NaCl, pH 6.8) were mixed with 1 ml of a solution containing the maleoylated carrier proteins (2.5 mg/ml) in 50 mM sodium phosphate, 250 ml NaCl, pH 6.8 and incubated for 2 h at 4° C. and further 4 h at RT. Unreacted maleimid groups were blocked by addition of 2-mercaptoethanole up to a concentration of 10 mM and over night incubation at 4° C. The resulting conjugate was dialysed against 10 mM sodium phosphate, 150 mM NaCl, pH 7.5 at 4° C. (3 times buffer exchange, MW cut-off 10.000).

Immunization

Five mice were immunized intraperitoneally for 39 days. For immunization, a water-in-oil emulsion consisting of equal parts of the antigen solution (consisting of equal parts of the three different peptide-BTG-conjugates) and complete or incomplete Freundt's adjuvants was used.

Fusion

Three of the immunized mice were sacrificed by CO2 incubation. Spleens were taken and homogenized under sterile conditions. Spleen cells and myeloma SP2/0 cells were washed several times in Dulbecco's Modified Eagle Medium (DMEM, SIGMA) and fused in the ratio of 2,3 spleen cells: 1 SP2/0 cell using polyethylenglycole 3350 (1 ml 50% (w/v)). Further handling of the fused hybridomas was performed according to standard methodologies.

ELISA

An IgG directed ELISA was used to screen the cell culture supernatant. The test was performed in 96-well polystyrol microtiter plates (Greiner, Cat. No. 655061). The plates were coated with the BSA-pGlu-6166 peptide. 100 µl undiluted cell culture supernatant was added to each well and incubated for 1 h at RT. Supernatant from SP2/0 cells was used as negative control. Supernatant from the spleen cells was used as positive control.

Positive wells were detected using goat-anti-mouse IgG, which was conjugated with alkaline phosphatase. The optical density (OD) was measured in a Dynex Opsys MR Microplate Reader at 405 nm.

Selection of stable antibody producing hybridoma cells

Cells from positive wells were transferred to 24-well plates and cultivated for several days. Cells were again transferred and tested for BSA-pGlu-6199 binding and cross-reactivity in the ELISA. Positive wells were used for cryo-conservation of the hybridoma cell lines.

Cloning Via Limited Dilution

Two consecutive cloning steps were performed in order to separate antibody producing cells from non-producing cells and to assure that the selected cells are monoclonal. Both cloning steps were performed according to the method of limited dilution.

Cryoconservation

Selected hybridomas were cryo-conserved using DMSO and standard methods.

1.2. ELISA Assays

Capturing of Aβ N3pE-40 was performed using hAβ (x-40) ELISA (HS) from TGC (The GENETICS Company; Switzerland), basically according to the manufacturer's instructions.

Biotinylated detection antibodies for Aβ N3pE (pGlu-6166) were generated. Where indicated, IBL HRP-conjugated Aβ N3pE antibody was used as positive control (available only in combination with the IBL ELISA Human Amyloid β (N3pE) Assay Kit). Corresponding Aβ N3pE-40 peptides (50 µg aliquots in Hexafluoroisopropanol (HFIP) stored at −80° C.) were synthesized. Shortly before use, HFIP was evaporated and the peptide was diluted with 100 mM Tris/HCl pH 10, 4 to 1 µg/µl. This stock solution was diluted further with TGC antibody diluent. Subsequent capturing and detection was carried out according to manufacturer's instructions.

1.3. PepSpot™ Analysis

Specificity and biological integrity of Aβ N3pE antibodies and cell culture supernatants was determined by using the PepSpot™ technology of JPT Peptide Technologies GmbH, Volmerstrasse 5 (UTZ), 12489 Berlin, Germany.

Corresponding PepSpot™ membranes were prepared at JPT. The principle of this method was introduced and described before by Kramer et al. 1997 Cell 91, 799-809.

For analysis, membranes were blocked for two hours with TBST-M (10 mM Tris-Hcl, pH 7.5, 150 mM NaCl, 0.005% Tween20+5% skimmed milk) at room temperature with gentle shaking. Membranes were incubated over night at 4° C. on a rocking platform with the individual cell culture supernatants diluted in equal volumes of TBST-M. Secondary anti-mouse antibody conjugated with alkaline phosphatase was used for signal detection, following standard procedures.

1.4. DotBlot Analysis

A simple DotBlot protocol was accomplished to obtain information about the sensitivity of Aβ N3pE antibody and cell culture supernatants towards the respective native peptide. To that end, Aβ N3pE-40 peptide in descending concentrations (1000 ng-8 ng) was spotted onto small pieces of nitrocellulose membrane, and subsequent experimental procedure was performed as for the PepSpot™ membranes.

1.5. SDS PAGE

12% SDS Polyacrylamide gels were cast following standard protocols. 15 µl of cell culture supernatants and 10 µg of biotinylated antibody were separated on a 12% SDS polyacrylamide gel. Electrophoresis was carried out for 2 hours at 100 V constant.

1.6. BIACORE Analysis

Aβ N3pE-40 peptide (positive control) and Aβ N3E-40 peptide (negative control) were coupled on a Biacore CM5 Chip. Unmodified chips are used to determine blank values. Association and dissociation of biotinylated antibody diluted from 20 µg/ml to 1 µg/ml in TGC diluent was monitored to allow for subsequent determination of the respective KD value. In this way also binding characteristics of the individual cell culture supernatants were determined.

1.6.1 Affinity of AβN3pE Specific Antibody Clone 6-1-6 and 24-2-3

The purified antibody clone 6-1-6 was diluted in HBS-EP buffer (Biacore) down to 100, 50, 30, 20, 15, 10, 7, 4, 2, 1 nM. The affinity was determined using a Biacore 3000 with CM5-Chip, on which AβpE3-40 was immobilized. The system was run with 30 μl/min. Measured bulk effects and unspecific binding to the chip surface were corrected by subtraction of the signal of flow cell 4, at which AβpE3-40 was immobilized, and the empty flow cell 3. The association (10 min) was obtained by injection of 300 μl of each concentration. The dissociation was observed over 10 min. Remaining antibody molecules were removed by injection of 5 μl 0.1 M HCL. For every antibody concentration the association and dissociation was recorded. The determination of the association and dissociation rate and the dissociation constant was performed by a global simultaneously fit of association and dissociation phase for all recorded antibody concentrations using the "Bivalent analyte" model.

1.7. Sequencing Antibody Variable Regions

Cultivation of Hybridoma Cells:

Hybridoma cells were grown in D-MEM (+L-Glutamin, +Na-Pyruvat, 4, 5 g/l Glucose, Gibco) with the addition of 15% FBS, 1% MEM-NEA (non essential amino acids, Gibco), 50 μg/ml Gentamycin (Gibco) and 50 μM β-mercaptoethanol at 37° C. and 5% $CO_2$. Subcultivation occurred after 3-4 days depending on cell density. Cells were seeded in a concentration of $0.5 \times 10^6$ cells/ml, splitting occurred at a cell density of $2\text{-}5 \times 10^6$ cells/ml.

cDNA Synthesis and Reverse Transcription:

Total RNA was isolated from $2 \times 10^6$ cells according to the manual of the NucleospinRNA Isolation Kit (Macherey-Nagel). 100 ng RNA were applied for cDNA synthesis by using Oligo $(dT)_{15}$ primer (Promega) and SuperScript III Reverse Transcriptase (Invitrogen).

PCR-Amplification of Heavy and Light Chain Variable Regions:

Heavy chain variable regions were amplified from the template cDNA by using Phusion™ High-Fidelity DNA Polymerase (NEW ENGLAND BioLabs) with the primer MHCG1 (in case of clone 5-5-6 and 6-1-6) and MHCG2b (clone 17-4-3 and 24-2-3) in combination with primers MHV1-12. For amplification of light chain variable regions the primer MKC in combination with the primers MKV1-MKV11 were used. Primer sequences are shown in table 1.

Cloning of PCR Products in pJET1.2:

Heavy and light chain variable regions, amplified by PCR, were cloned into pJET1.2/blunt vector according to the protocol of CloneJET™ PCR Cloning Kit (Fermentas). Sequencing occurred with pJET1.2 sequencing primers.

TABLE 1

Primer sequences for PCR-amplification of heavy and light chain variable regions

| Name | Sequence | SEQ ID NO. |
|---|---|---|
| MKV1 | ATGAAGTTGCCTGTTAGGCTGTTGGTGCTG | 23 |
| MKV2 | ATGGAGWCAGACACACTCCTGYTATGGGTG | 24 |
| MKV3 | ATGAGTGTGCTCACTCAGGTCCTGGSGTTG | 25 |
| MKV4 | ATGAGGRCCCCTGCTCAGWTTYTTGGMWTCTTG | 26 |

TABLE 1-continued

Primer sequences for PCR-amplification of heavy and light chain variable regions

| Name | Sequence | SEQ ID NO. |
|---|---|---|
| MKV5 | ATGGATTTWCAGGTGCAGATTWTCAGCTTC | 27 |
| MKV6 | ATGAGGGTKCYYTGYTSAGYTYCTGRGG | 28 |
| MKV7 | ATGGGCWTCAAGATGGAGTCACAKWYYCWGG | 29 |
| MKV8 | ATGTGGGGAYCTKTTTYCMMTTTTTCAATTG | 30 |
| MKV9 | ATGGTRTCCWCASCTCAGTTCCTTG | 31 |
| MKV10 | ATGTATATATGTTTGTTGTCTATTTCT | 32 |
| MKV11 | ATGGAAGCCCCAGCTCAGCTTCTCTTCC | 33 |
| MKC | ACTGGATGGTGGGAAGATGG | 34 |
| MHV1 | ATGAAATGCAGCTGGGGCATSTTCTTC | 35 |
| MHV2 | ATGGGATGGAGCTRTATCATSYTCTT | 36 |
| MHV3 | ATGAAGWTGTGGTTAAACTGGGTTTTT | 37 |
| MHV4 | ATGRACTTTGGGYTCAGCTTGRTTT | 38 |
| MHV5 | ATGGACTCCAGGCTCAATTTAGTTTTCCTT | 39 |
| MHV6 | ATGGCTTGTCYTRGSGCTRCTCTTCTGC | 40 |
| MHV7 | ATGGRATGGAGCKGGRTCTTTMTCTT | 41 |
| MHV8 | ATGAGAGTGCTGATTCTTTTGTG | 42 |
| MHV9 | ATGGMTTGGGTGTGGAMCTTGCTATTCCTG | 43 |
| MHV10 | ATGGGCAGACTTACATTCTCATTCCTG | 44 |
| MHV11 | ATGGATTTTGGGCTGATTTTTTTTATTG | 45 |
| MHV12 | ATGATGGTGTTAAGTCTTCTGTACCTG | 46 |
| MHCG1 | CAGTGGATAGACAGATGGGGG | 47 |
| MHCG2b | CAGTGGATAGACTGATGGGGG | 48 |

1.8 Application of Antibody Clone 6-1-6 for N3pE ELISA

A 96-well maxisorb plate (Nunc) was coated with capture antibody by incubation of 100 μl per well of 2 μg/ml anti-Aβ antibody 4G8, diluted in D-PBS, overnight at 4° C. The plated was sealed. The coating solution was removed and the surface of the plate was blocked with 200 μl per well PIERCE Protein-free ELISA-Blocker (without Tween-20) for 2 hours at room temperature. Afterwards the plate was washed with 6-times with TBS+0.05% (v/v) Tween-20. Remaining washing solution was removed by tapping of the plate. The AβpE3-40 standard peptide was diluted in PIERCE Protein-free ELISA-Blocker (with Tween-20) down to 200, 100, 50, 25, 12.5, 6.25, 3.125 pg/ml. 100 μl of every concentration and 100 μl of dilution buffer (Blank) were pipetted on the plate. The plate was sealed and incubated at 4° C. for 2 hours. Afterwards the plate was washed 6-times with TBS+0.05% (v/v) Tween-20. Remaining washing solution was removed by tapping of the plate. 100 μl of the detection antibody-enzyme conjugate solution, which contains 1 μg/ml AβN3pE specific antibody clone 6-1-6 and 2 pg/ml Streptavidin-HRP conjugate (Sigma) solved in PIERCE Protein-free ELISA-Blocker (with Tween-20), was pipetted in each well. The plate was sealed and incubated at 4° C. for 1 hour. Afterwards the plate was washed 6-times with TBS+0.05% (v/v) Tween-20. Remaining washing solution is removed by tapping of the plate. In every well 100 μl SureBlue substrate solution (KPL) are pipetted and the plate was incubated in the dark at room temperature for 30 min. The reaction was stopped by addition of 100 μl per well of 1 M $H_2SO_4$. The absorbance was measured with TECAN Sunrise at 450 nm corrected by the absorbance at 540 nm.

1.9 Investigation of Cross Reactivity, Analyzed Via ELISA and Surface-Plasmon-Resonance (SPR)

ELISA:

A 96-well maxisorb plate (Nunc) was coated with capture antibody by incubation of 100 μl per well of 2 μg/ml anti-Aβ antibody 4G8, diluted in D-PBS, overnight at 4° C. The plated was sealed. The coating solution was removed and the surface of the plate was blocked with 200 μl per well PIERCE Protein-free ELISA-Blocker (without Tween-20) for 2 hours at room temperature. Afterwards the plate was washed with 6-times with TBS+0.05% (v/v) Tween-20. Remaining washing solution was removed by tapping of the plate. The AβpE3-40 standard peptide and other Aβ-Peptides (2-40, 3-40, 4-40, 1-42, 3-42 and pE11-40) were diluted in PIERCE Protein-free ELISA-Blocker (with Tween-20) down to 800, 400, 200, 100, 50, 25, 12.5. 100 μl of every concentration and 100 μl of dilution buffer (Blank) were pipetted on the plate. The plate was sealed and incubated at 4° C. for 2 hours. Afterwards the plate was washed 6-times with TBS+0.05% (v/v) Tween-20. Remaining washing solution was removed by tapping of the plate. 100 μl of the detection antibody-enzyme conjugate solution, which contains 1 μg/ml AβN3pE specific antibody clone 6-1-6 and 2 μg/ml Streptavidin-HRP conjugate (Sigma) diluted in PIERCE Protein-free ELISA-Blocker (with Tween-20), was pipetted in each well. The plate was sealed and incubated at 4° C. for 1 hour. Afterwards the plate was washed 6-times with TBS+0.05% (v/v) Tween-20. Remaining washing solution was removed by tapping of the plate. In every well 100 μl SureBlue substrate solution (KPL) were pipetted and the plate was incubated in the dark at room temperature for 30 min. The reaction was stopped by addition of 100 μl per well of 1M $H_2SO_4$. The absorbance was measured with TECAN Sunrise at 450 nm corrected by the absorbance at 540 nm.

SPR:

Beside different Aβ species also the cross reactivity to other pGlu-Peptide, which occur in the human body, was determined. This was made by surface plasmon resonance. Following peptides or there N-terminal region of them were immobilized on the surface of CM5-Chips:

MCP1, MCP2, big gastrin, gonadoliberin, neurotensin, orexin A, fibronectin, collagen 1 and TRH. As positive control also the binding to AβpE3-40 was analyzed. The N3pE antibody clones 6-1-6 and 24-2-3 were diluted in HBS-EP (Biacore) down to 25 μg/ml. The binding was observed using a Biacore 3000 with several CM5-Chips, on which the respective peptides (on flow cell 2, 3 and 4 was immobilized. The system was run with 20 μl/min. Measured bulk effects and unspecific binding to the chip surface were corrected by subtraction of the signal of flow cell 2, 3 and 4, at which the tested peptides was immobilized, and the empty flow cell 1. The association (9 min) was obtained by injection of 180 μl of antibody clones 6-1-6 and 24-2-3, respectively. The dissociation was observed over 9 min. Remaining antibody molecules were removed by injection of 5 μl 0.1 M HCL. For every interaction of the antibody with the different peptides the association and dissociation was recorded. The cross reactivity was determined by evaluation of the association phase concerning rate and signal at the end. The values for all pGlu-Peptides compared with the signal for AβpE3-40.

1.10 Optimization and Validation of N3pE ELISA for Brain Analysis

Our developed N3pE ELISA should be used for analysis of AβpE3-42 concentration in brain of transgenic mice. Generally, hemisphere and brainstem were separately analyzed concerning AβpE3-42 content. Mouse brain was homogenized in 500 μl 2-SDS solution with protease inhibitor in Precelly (Peqlab) homogenizer using ceramic beads. The suspension was pipetted off from the beads and transferred into centrifuge tube. Beads were washed again with 250 μl 2-SDS solution with protease inhibitor and solution transferred into the centrifuge tube. The 750 μl SDS brain suspension was sonicated on crashed ice for 20 sec. The sample was centrifuged for 1 hour at 4° C. with 75000×g. Afterwards the supernatant was removed, aliquoted and stored until ELISA analysis at −80° C. The remaining SDS insoluble pellet was mixed with 150 μl 70% formic acid and sonicated on crashed ice for 20 sec. Immediately after sonification the solution was neutralized with 2850 μl 1 M Tris, which was the old method, or 2850 μl EIA buffer (PBS+10 mg/ml BSA+0.05% Tween-20)+860 μl 3.5 M Tris for neutralization, representing the new method. The formic acid fraction samples were stored until ELISA at −80° C.

The N3pE ELISA was performed by following protocol:

A 96-well maxisorb plate (Nunc) was coated with capture antibody by incubation of 100 μl per well of 2 μg/ml anti-Aβ antibody 4G8, diluted in D-PBS, overnight at 4° C. The plated was sealed. The coating solution was removed and the surface of the plate was blocked with 200 μl per well PIERCE Protein-free ELISA-Blocker (without Tween-20) for 2 hours at room temperature. Afterwards the plate was washed with 6-times with TBS+0.05% (v/v) Tween-20. Remaining washing solution was removed by tapping of the plate. The AβpE3-42 standard peptide was diluted in PIERCE Protein-free ELISA-Blocker (with Tween-20) (old method) or EIA buffer (new method) down to 1029.2, 514.6, 257.3, 128.65, 64.32, 31.16, 16.08 μg/ml. 100 μl of every concentration and 100 μl of dilution buffer (Blank) were pipetted on the plate. The SDS samples were thawed, diluted 1:25 and 1:100, respectively, in PIERCE Protein-free ELISA-Blocker (with Tween-20) (old method) or EIA buffer (new method) and pipetted on ELISA plate. The formic acid samples (old method: formic acid/Tris; new method: formic acid/EIA buffer/Tris) were thawed and undiluted pipetted on ELISA plate. The plate was sealed and incubated at 4° C. for 2 hours. Afterwards the plate was washed 6-times with TBS+0.05% (v/v) Tween-20. Remaining washing solution was removed by tapping of the plate. 100 μl of the detection antibody-enzyme conjugate solution, which contains 1 μg/ml AβN3pE specific antibody clone 6-1-6 and 2 μg/ml Streptavidin-HRP conjugate (Sigma) solved in PIERCE Protein-free ELISA-Blocker (with Tween-20), was pipetted in each well. The plate was sealed and incubated at 4° C. for 1 hour. Afterwards the plate was washed 6-times with TBS+0.05% (v/v) Tween-20. Remaining washing solution was removed by tapping of the plate. In every well 100 μl SureBlue substrate solution (KPL) are pipetted and the plate was incubated in the dark at room temperature for 30 min. The reaction was stopped by addition of 100 μl per well of 1 M $H_2SO_4$. The absorbance was measured with TECAN Sunrise at 450 nm corrected by the absorbance at 540 nm.

1.11 Application of N3pE Antibody Clones for Immunohistochemistry

Formalin-fixed and paraffin-embedded sections from human brain (cortex) were treated as follows:
1. Deparaffinizing and rehydrating sections (immobilized on slides):
   a. Incubation of slides in Histoclear or xylene for 3 minutes
   b. Remove cleaning solution
   c. Incubation of slides again in Histoclear or xylene for 3 minutes
   d. Incubation of slides in Histoclear or xylene 1:1 with 100% ethanol for 3 minutes
   e. Incubation of slides in 100% ethanol for 3 minutes, remove solution
   f. Incubation of slides again in 100% ethanol for 3 min
   g. Incubation of slides in 95% ethanol for 3 minutes
   h. Incubation of slides in 70% ethanol for 3 minutes
   i. Incubation of slides in 50% ethanol for 3 minutes
   j. Incubation of slides in distilled water for 3 minutes
2. Quenching endogenous peroxidase activity:
Incubation of slides with 99 ml methanol+1 ml 30% hydrogen peroxide for 10 minutes at room temperature.
3. Washing the slides with water: 2×5 minutes
4. Removing water in individual slides and place slides on slide rack in a humidity chamber to prevent sections from drying. Cover section with 88% formic acid at room temperature for 10 minutes under fume hood. Rinse in water several times and allow to shake in a water-filled staining dish for 10 minutes.
5. Blocking in 10% horse serum for 20 minutes at room temperature.
6. Shaking off (or aspirate) blocking solution and apply primary antibody (N3pE antibody clone 6 or 24) for overnight at 4° C.
7. Washing slides separately with TBS for 10 minutes to avoid dragging from one slide to another.
8. Addition of biotinylated secondary antibody (goat anti-mouse from Vector Laboratories): 9 ml TBS, 1 ml goat serum, 45 µl $2^{nd}$ antibody). Incubate 30 minutes at room temperature.
9. Washing slides separately with TBS for 10 minutes to avoid dragging from one slide to another.
10. Addition of ABC-solution (10 ml TBS, 100 µl horse serum, 90 µl component A, 90 µl component B). Incubate 30 minutes at room temperature.
11. Washing slides with 50 mM Tris: 2×10 minutes
12. Color reaction: Incubation of sections with DAB solution (20 mg DAB from Sigma in 100 ml 50 mM Tris, filtered, and add 33 µl 33% hydrogen peroxide). Using microscope to observe color reaction. The reaction product is brown colored. Stop the reaction by putting slides into staining dishes containing water.
13. Washing slides with water for 10 minutes
14. Counterstaining with hematoxylin, washing with water.
15. Dehydrating and clearing: Follow step 1 in reverse order (e.g. water, ethanols to 100% histoclean)
16. Coverslip with permount (Fisher Scientific). Drying slides on air. Clean slides with razor blade and ethanol.

2. Results 2.1 Production of Antibodies

Six clones were isolated that stably produce antibodies against the pGlu-6166-BSA peptide: clones 1-8-12, 5-5-6, 6-1-6, 12-1-8, 17-4-3 and 24-2-3. These clones were subject to further characterization.

2.2. Determination of Required Antibody Concentration:

The intensity of signals in the ELISA assays correlates not only with the concentration of analyte/Aβ variant but is also strongly dependent on the concentration of deployed antibody. Since Aβ variants are only present in low concentration in serum samples it is necessary to determine antibody concentrations that are able to detect low concentrations of the corresponding Aβ variants. Commercially available Aβ ELISA kits have a specified detection limit towards Aβ in the low pg range. In standard curves the highest concentration is usually 500 pg/ml. General information about deployed antibody concentration is typically lacking in data sheets/instruction manuals, however, due to further information as derivable from the general literature 1 µg/ml of antibody is used as default.

Figure 1A:
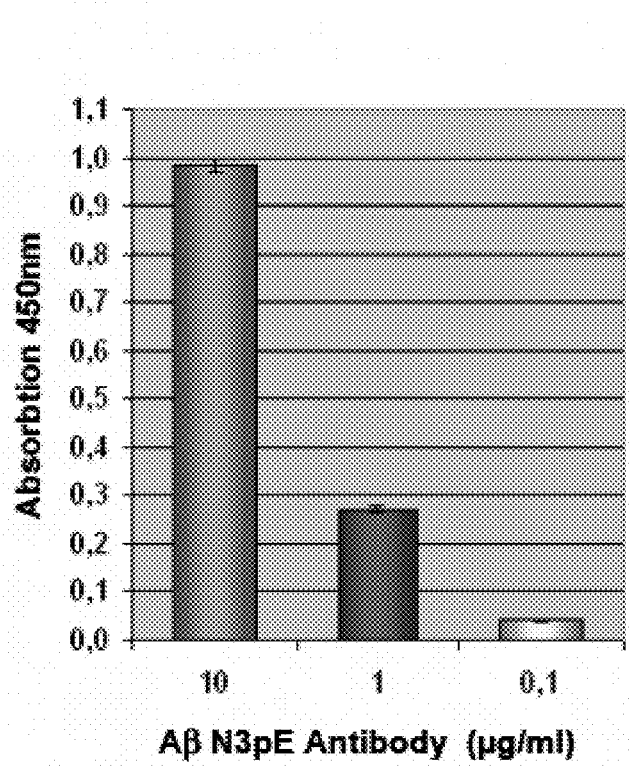
FIG. 1A
Figure 1B:
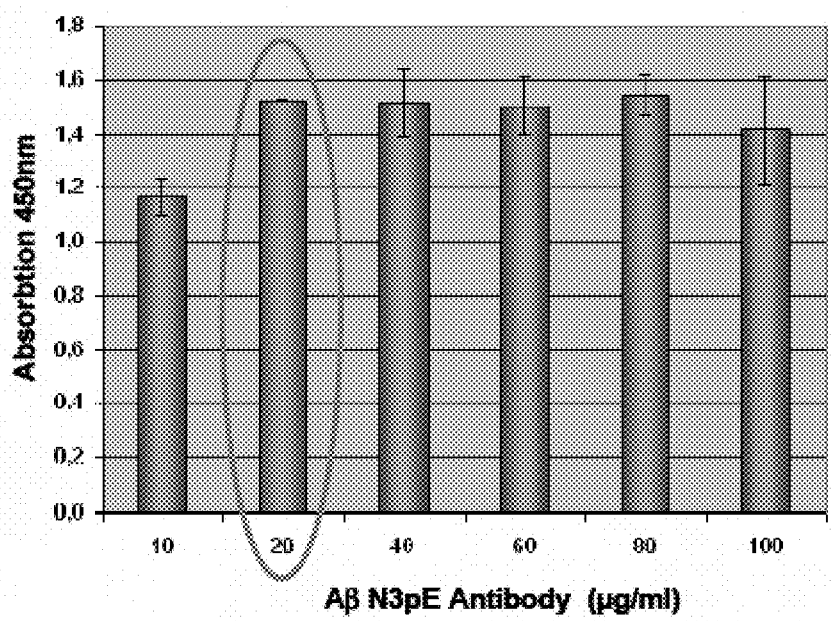

In a first series of experiments it was not possible to detect 500 pg/ml Aβ N3pE-40 with the corresponding pGlu-6166 12-1 biotin-conjugated antibody. In fact, relatively high Aβ N3pE concentrations (10 ng/ml) were required to obtain signals with 1 µg/ml antibody (see FIG. 1A: middle bar). The intensity of this signal was tremendously enhanced by increasing the antibody concentration to 10 µg/ml (see FIG. 1A: left-hand bar). Until 20 µg/ml antibody the intensity of signal can be further elevated (see FIG. 1B). Beyond this concentration no further increase in signal intensity can be achieved. Therefore, 20 µg/ml antibody was used to determine the detection limit for the pGlu-6166 antibody.

2.3. DotBlot Analysis

The Aβ N3pE-x antibody pGlu-6166 was chosen in the screening process because the original cell clone (designated 12-1-8) exhibited strong binding towards the peptide taken for immunization and very low cross reactivity (see table 2).

TABLE 2

Screening results demonstrating signals in ELISA assays obtained with several hybridoma cell clone supernatants.

| Clone | N3pE-BSA | isoDAE-BSA | N3E-BSA | N11E-BSA | N11pE-BSA |
|---|---|---|---|---|---|
| 1-8-12 | 1.787 | 0.012 | 0.142 | 0.011 | 0.005 |
| 5-5-6 | 1.649 | 0.015 | 0.126 | 0.004 | 0.006 |
| 6-1-6 | 1.377 | 0.013 | 0.125 | 0.007 | 0.014 |
| 12-1-8 | 2.123 | 0.005 | 0.009 | 0.001 | 0.005 |
| 17-4-3 | 1.915 | 0.007 | 0.320 | 0.003 | 0.004 |
| 24-2-3 | 1.768 | 0.014 | 0.218 | 0.003 | 0.002 |
| positive control | 1.824 | 1.227 | 1.596 | 1.243 | 1.346 |
| negative control | 0.045 | 0.005 | 0.008 | 0.001 | 0.003 |

No screening step, dealing with the full length, native Aβ N3pE-40 peptide had been included so far. Therefore the pool of available pGlu6166 hybridoma cell clones was screened for clones expressing antibodies which might exhibit a higher affinity for the native Aβ N3pE-40 peptide.

Figure 2:
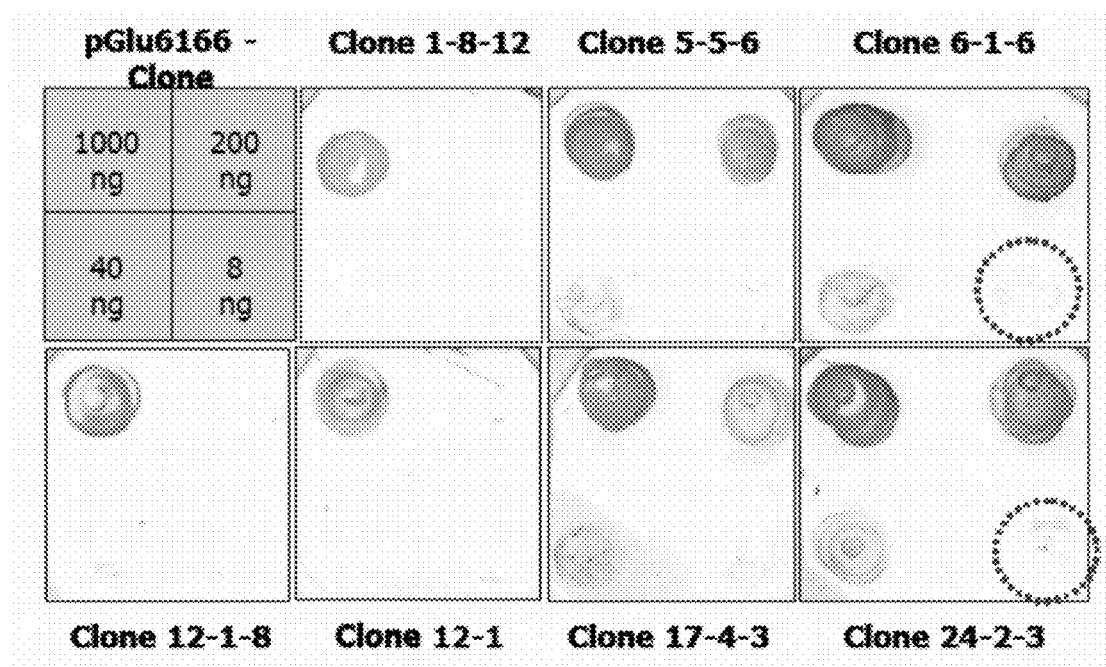

As seen in FIG. 2, cell clones could be identified which indeed exhibit higher sensitivity towards the native full length Aβ N3pE-40 peptide. Whereas the pGlu-6166 antibody clone 12-1 could only detect 1 µg peptide, clones 6-1-6 and 24-2-3 also gave signals with as little as 8 ng peptide. Hence, clones 6-1-6 and 24-2-3 are 125 times more sensitive. With these clones, a detection limit of 8 µg/ml Aβ N3pE-40 peptide in a corresponding ELISA could be attainable.

2.4. PepSpot Analysis

Figure 3:
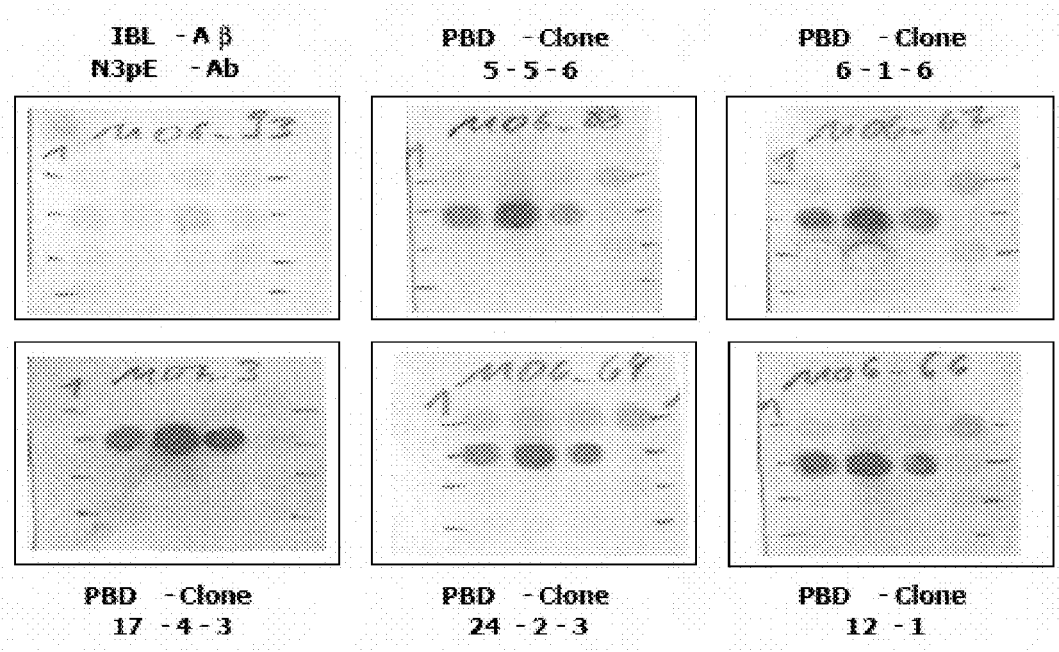

Specificity was checked next by PepSpot analysis to compare biotinylated Aβ N3pE-x antibody pGlu-6166 with hybridoma cell clones. In table 3, all peptides are listed which correspond to spots on the PepSpot membrane. As seen in FIG. 3 pGlu-6166 clones 6-1-6 and 24-2-3 do not produce more cross signals than pGlu-6166 antibody clone 12-1. All clones investigated recognized primarily spot number 6—the specific Aβ N3pE-x spot (pEFRHD..., i.e. SEQ ID No: 12), followed by spots number 5 (EFRHD... SEQ ID No: 11) and 7 (FRHD... SEQ ID No: 13). A faint signal was also attained with spot number 4 (AEFRHD... SEQ ID No: 10).

value of 30 nM. A comparison of the hybridoma cell clone supernatant 12-1 with cell clone supernatant 6-1-6 revealed striking differences in binding characteristics. The association of clone 6-1-6 was approximately 5 times higher than that observed with clone 12-1. Most markedly, however, is the difference in dissociation behavior. Whereas clone 6-1-6 hardly dissociates from the Aβ N3pE-40 peptide, 12-1 is readily washed off within a few minutes. Hence, the poor

TABLE 3

Sequences of Aβ peptides spotted onto PepSpot ™ Membranes (JPT Peptide Technologies GmbH) and detection by pGlu-6166 hybridoma cell clones

| No. | Peptide Sequence Aβ 1-40 (SEQ ID No: 2)<br>--DAEFRHDSGYEVHHQKLVFFAEDVGSNKGAIIGLMVGGVV | IBL-AK | 5-5-6 | 6-1-6 | 17-4-3 | 24-2-3 | 12-4 | SEQ ID No. |
|---|---|---|---|---|---|---|---|---|
| 1 | KMDAEFRHDSGYE | − | − | − | − | +/− | − | 7 |
| 2 | DAEFRHDSGYEVH | − | − | − | − | +/− | − | 8 |
| 3 | iDAEFRHDSGYEVH | − | − | − | − | +/− | − | 9 |
| 4 | AEFRHDSGYEVHH | − | +/− | +/− | − | +/− | +/− | 10 |
| 5 | EFRHDSGYEVHHQ | − | + | + | + | + | + | 11 |
| 6 | pEFRHDSGYEVHHQ | − | +++ | +++ | +++ | +++ | +++ | 12 |
| 7 | FRHDSGYEVHHQK | + | + | + | + | + | + | 13 |
| 8 | GYEVHHQKLVFFA | − | − | − | − | − | − | 14 |
| 9 | EVHHQKLVFFAED | − | − | − | − | − | − | 15 |
| 10 | pEVHHQKLVFFAED | − | − | − | − | − | − | 16 |
| 11 | VHHQKLVFFAEDV | − | − | − | − | − | − | 17 |
| 12 | DAEFRHiDSGYEVH | − | − | − | − | − | − | 18 |
| 13 | iDSGYEVHHQKLVF | − | − | − | − | − | − | 19 |
| 14 | LVFFAEDVGSNKG | − | − | − | − | − | − | 20 |
| 15 | GSNKGAIIGLMVG | − | − | − | − | − | − | 21 |
| 16 | AIIGLMVGGVV | − | − | − | − | − | − | 22 | pE in table 3 means pGlu, pyroglutamate.
iD in table 3 means isoAsp, isoaspartate.

2.5. SDS-PAGE Analysis

Biological integrity of the Aβ-N3pE antibody and hybridoma cell culture supernatants was determined roughly by SDS-PAGE analysis (for details see Material & Methods supra).

Figure 4:
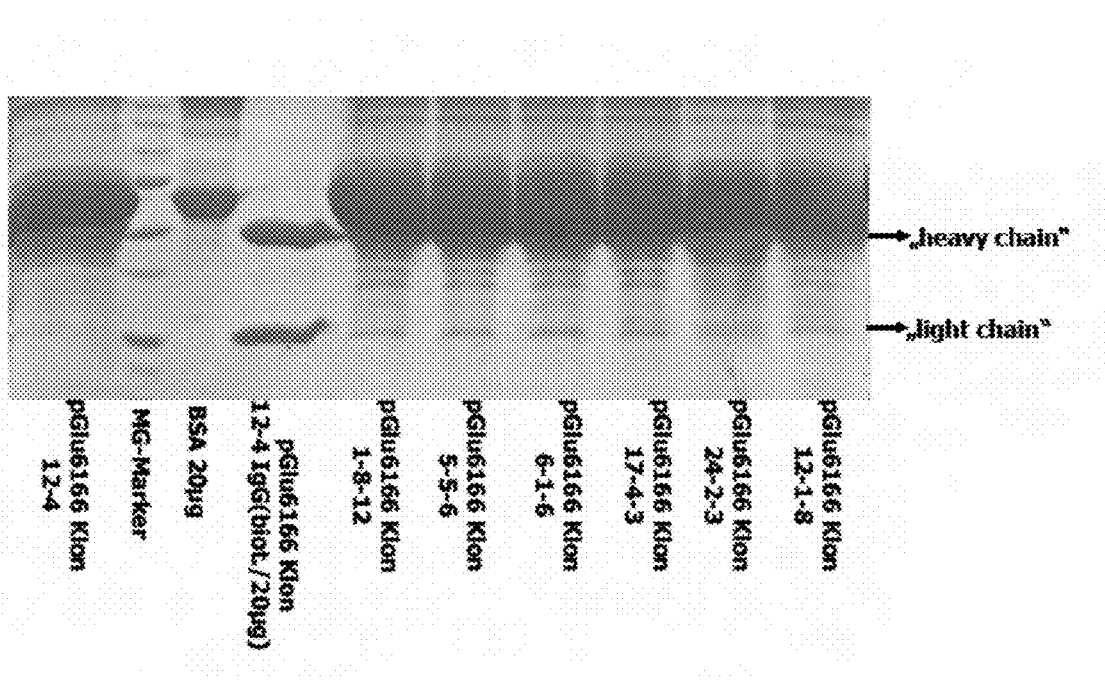

As seen in FIG. 4, all samples loaded onto the gel revealed sharp bands without smears, indicating the integrity of the pGlu-6166 12-1 antibody and the hybridoma cell clone supernatants.

2.6. BIACORE Analysis

With DotBlot analysis significant differences in sensitivity toward the Aβ N3pE-40 peptide of hybridoma cell clone supernatants compared to biotinylated pGlu-6166 antibody were diagnosed. However, with this method only an end point result is monitored. Biacore analysis on the other hand allows timewise resolution of the binding course of a given antibody. In order to check whether the poor binding of the pGlu-6166 12-1 antibody was a result of a low association to the Aβ N3pE-40 peptide, a Biacore analysis was performed as described in Materials and Methods, supra.

Figure 5:
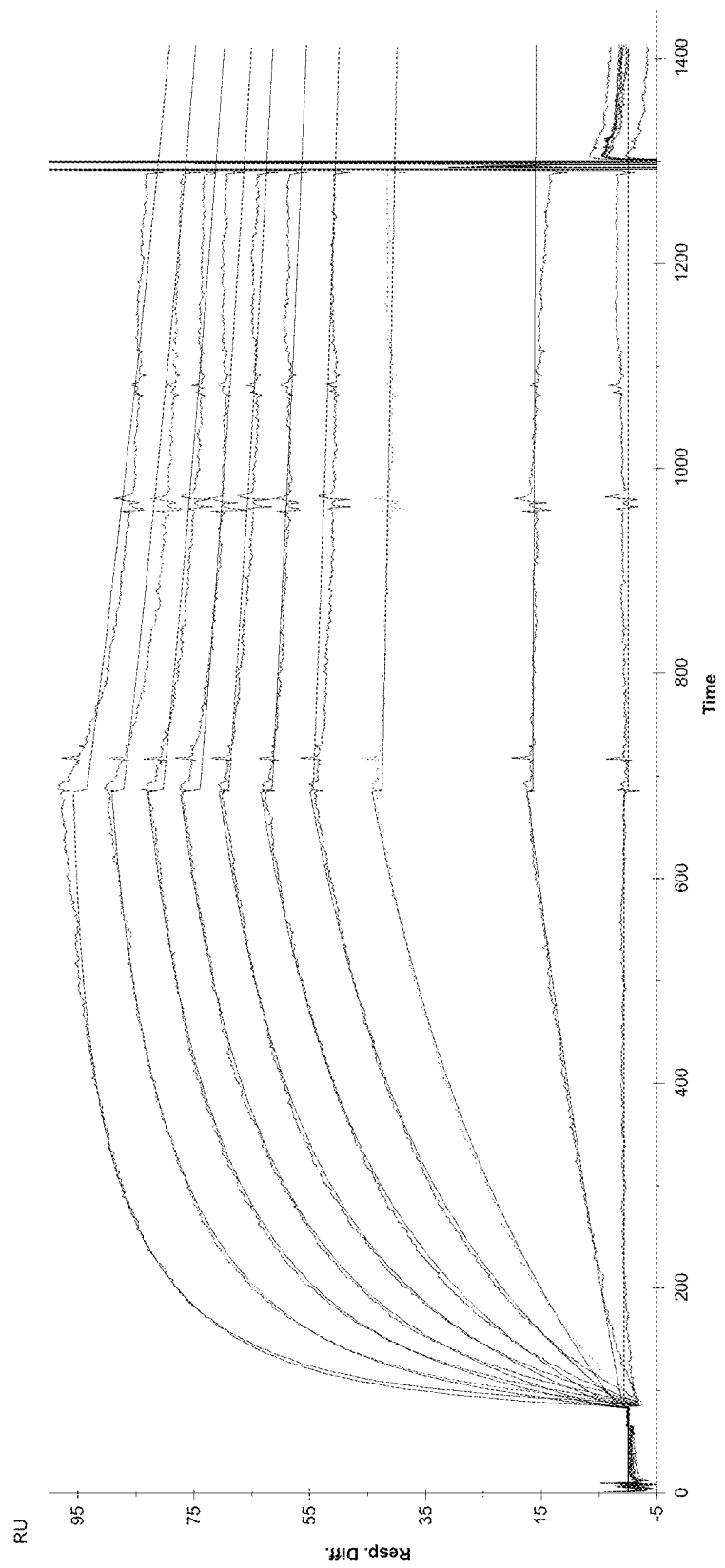

Monitoring binding courses of increasing concentrations of pGlu-6166 antibody allowed for calculation of a KD binding of clone 12-1 is very likely to be the consequence of the observed "off-rate". This assumption is further supported by the finding that clone 24-3-2, which gives particularly advantageous results in the DotBlot analysis, exhibits a very slow association to the Aβ N3pE-40 peptide but—in contrast to clone 12-1—has no observable "off-rate" (see also FIG. 5).

2.6.1 Affinity of AβN3pE Specific Antibody Clone 6-1-6 and 24-2-3

Figure 6:
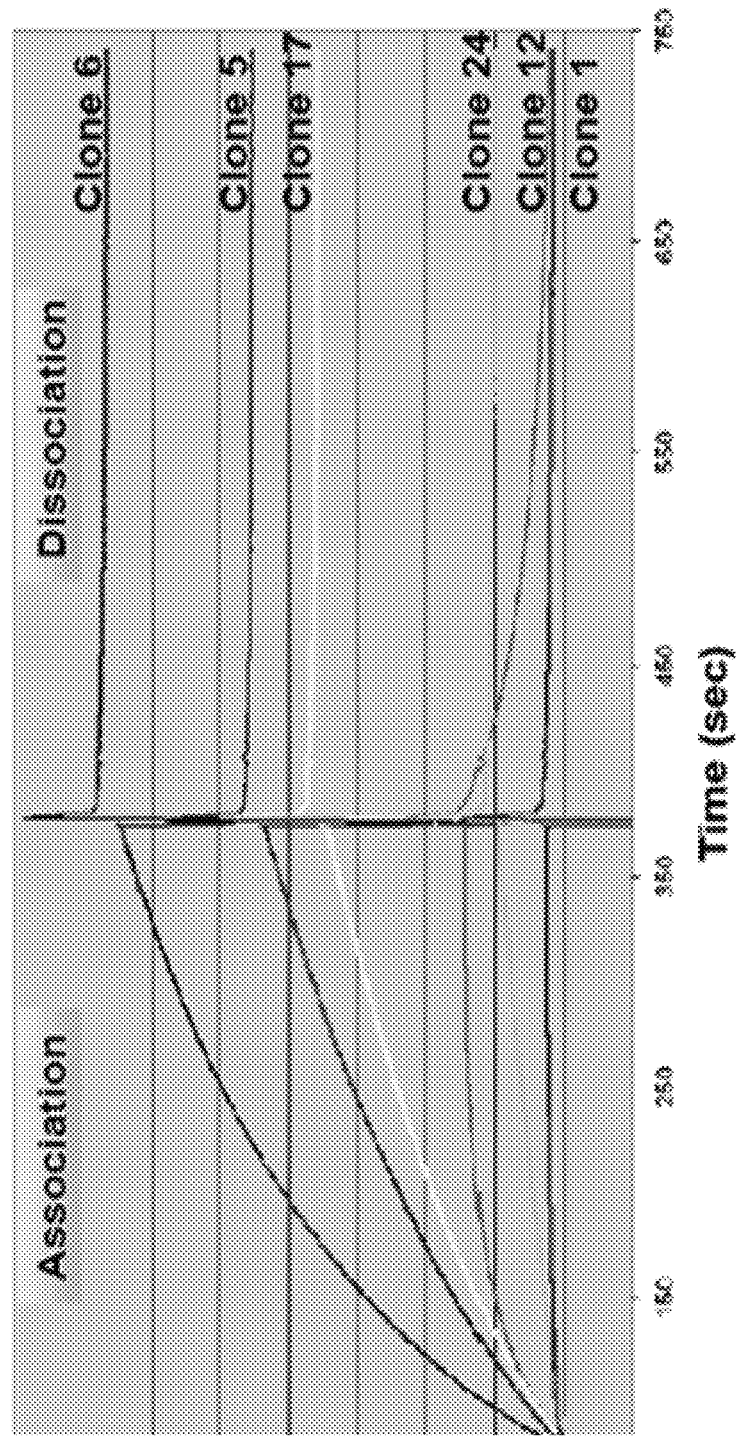

For N3pE antibody clone 6-1-6 the association rate, dissociation rate and dissociation constant was calculated by a global fit of all sensograms shown in FIG. 6.

The association rate was calculated with $1.67e5\ M^{-1}s^{-1}$, the dissociation rate with $2.63e-4\ s^{-1}$ and the dissociation constant with 1.57 nM.

Figure 7:
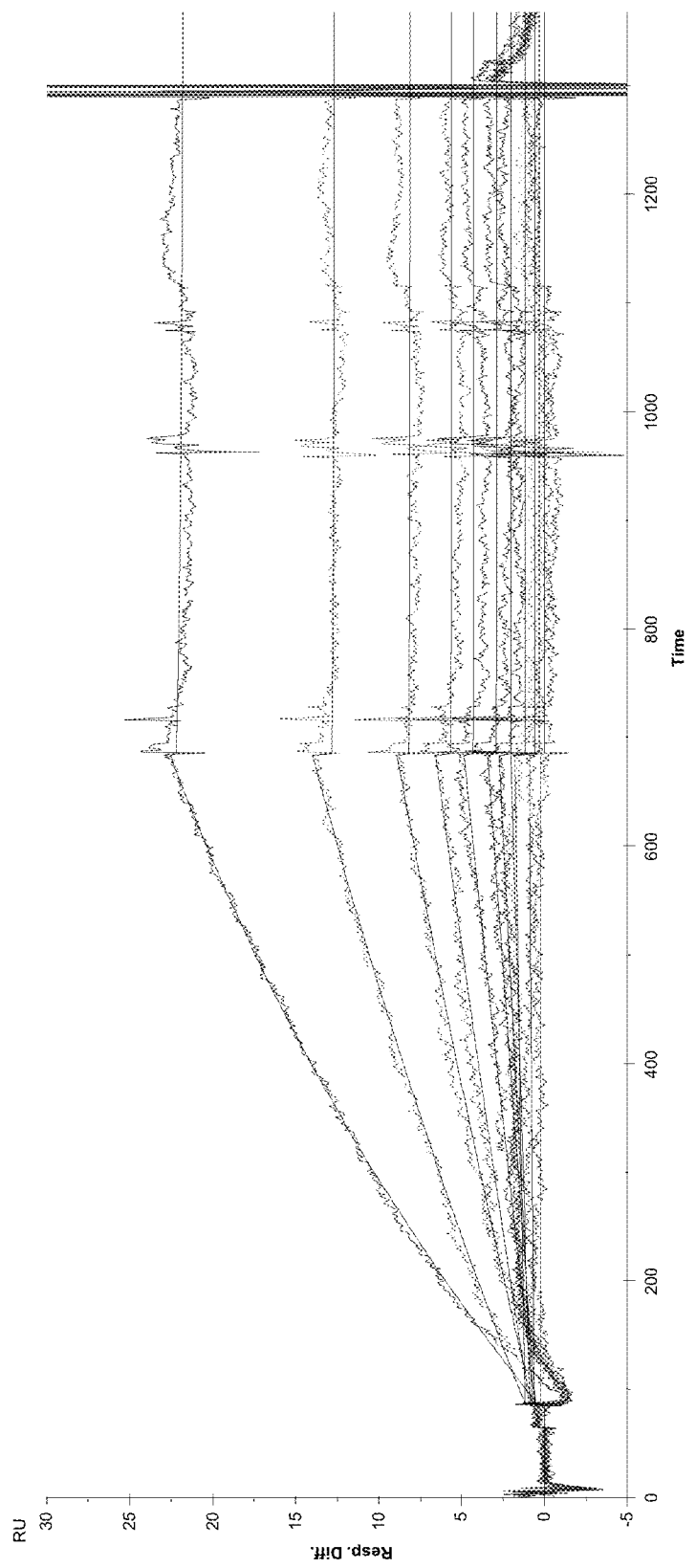

For N3pE antibody clone 24-2-3 the association rate, dissociation rate and dissociation constant was calculated by a global fit of all sensograms shown in FIG. 7.

The association rate was calculated with $3.25e3\ M^{-1}s^{-1}$, the dissociation rate with $3.29e-4\ s^{-1}$ and the dissociation constant with 101 nM.

2.7 Sequencing Antibody Variable Regions
The following sequences were identified:

2.7.1 Clone 5-5-6
Variable part light chain, nucleotide sequence
(SEQ ID NO: 49)
ATGGTGTCCTCAGCTCAGTTCCTGTTTCTGTTAGTGCTCTGGATTCAGGAAACCAACGGT

GATGTTGTGATGACCCAGACTCCACTCACTTTGTCGGTTACCATTGGACAACCAGCCTCT

ATCTCTTGCAAGTCAAGTCAGAGCCTCTTATATAGTGATGGAAAAACCTATTTGAATTGG

TTATTACAGAGGCCAGGCCAGTCTCCAATGCGCCTAATCTATCTGGTGTCTAAACTGGAC

TCTGGAGTCCCTGACAGGTTCACTGGCAGTGGATCAGGAACAGATTTTACACTGAAAATC

AGCAGAGTGGAGGCTGAGGATTTGGGAGTTTATTACTGCGTGCAAGGTACACATTTTCCA

TTCACGTTCGGCTCGGGGACAAAGTTGGAAATAAAACGGGCTGATGCTGCACCAACTGTA

TCCATCTTCCCACCAT

Variable part light chain, protein sequence
(SEQ ID NO: 50)
MVSSAQFLFLLVLWIQETNGDVVMTQTPLTLSVTIGQPASISCKSSQSLLYSDGKTYLNW

LLQRPGQSPMRLIYLVSKLDSGVPDRFTGSGSGTDFTLKISRVEAEDLGVYYCVQGTHFP

FTFGSGTKLEIKRADAAPTVSIFPP

Variable part heavy chain, nucleotide sequence
(SEQ ID NO. 51)
ATGGGATGGAGCGGGGTCTTTCTCTTCCTCCTGTCAGGAACTGCAGGTGTCCACTCTGAG

GTCCAGCTGCAACAGTCTGGACCTGAGCTGGTGAAGCCTGGAGCTTCAATGAAGATATCC

TGCAAGGCTTCTGGTTACTCATTCACTGGCTATACCATGAACTGGGTGAAGCAGAGCCAT

GGAAAGAACCTTGAGTGGATTGGACTTATTAATCCTTACAGTGGTGTTACTAGGTACAAC

CAGAAATTCAAGGGCAAGGCCACATTAATTGTAGACAAGTCATCCAGCACAGCCTACATG

GAGCTCCTCAGTCTGACATCTGAGGACTCTGCAGTCTATTATTGTACAAGAGAGGCTAAA

CGGGAGTGGGACGAGACTTACTGGGGCCAAGGGACTCTGGTCACTGTCTCTGCAGCCAAA

ACGACACCCCCATCTGTCTA

Variable part heavy chain, protein sequence
(SEQ ID NO: 52)
MGWSGVFLFLLSGTAGVHSEVQLQQSGPELVKPGASMKISCKASGYSFTGYTMNWVKQSH

GKNLEWIGLINPYSGVTRYNQKFKGKATLIVDKSSSTAYMELLSLTSEDSAVYYCTREAK

REWDETYWGQGTLVTVSAAKTTPPSV 2.7.2 Clone 6-1-6
Variable part light chain nucleotide sequence
(SEQ ID NO: 53)
ATGGTGTCCACAGCTCAGTTCCTGTTTCTGTTAGTGCTCTGGATTCAGGAAACCAACGGT

GATGTTGTGATGACCCAGACTCCACTCACTTTGTCGGTTACCATTGGACAACCAGCCTCT

ATCTCTTGCAAGTCAAGTCAGAGCCTCTTATATAGTGACGGAAAAACCTATTTGAATTGG

TTATTACAGAGGCCAGGCCAGTCTCCAATGCGCCTAATCTATCTGGTGTCTAAACTGGAC

TCTGGAGTCCCTGACAGGTTCACTGGCAGTGGATCAGGAACAGATTTTACACTGAAAATC

AGCAGAGTGGAGGCTGAGGATTTGGGAGTTTATTACTGCGTGCAAGGTACACATTTTCCA

TTCACGTTCGGCTCGGGGACAAAGTTGGAAATAAAACGGGCTGATGCTGCACCAACTGTA

TCCATCTTCCCACCATCCAG

Variable part light chain, protein sequence
(SEQ ID NO: 54)
MVSTAQFLFLLVLWIQETNGDVVMTQTPLTLSVTIGQPASISCKSSQSLLYSDGKTYLNW

LLQRPGQSPMRLIYLVSKLDSGVPDRFTGSGSGTDFTLKISRVEAEDLGVYYCVQGTHFP

FTFGSGTKLEIKRADAAPTVSIFPPS

Variable part heavy chain, nucleotide sequence
(SEQ ID NO: 55)
ATGGGATGGAGCGGGGTCTTTATCTTCCTCCTGTCAGGAACTGCAGGTGTCCACTCTGAGGTCC

AGCTGCAACAGTCTGGACCTGAGCTGGTGAAGCCTGGAGCTTCAATGAAGATATCCTGCAAGGC

TTCTGGTTACTCATTCACTGGCTACACCATGAACTGGGTGAAGCAGAGCCATGGAAAGAACCTT

GAGTGGATTGGACTTATTAATCCTTACAATGGTGTTACTAGGTACAACCAGAAGTTCAAGGGCA

AGGCCACATTAATTGTAGACAAGTCATCCAGCACAGCCTACATGGAGCTCCTCAGTCTGACATC

TGAGGACTCTGCAGTCTATTACTGTACAAGAGAGGCTAAACGGGAGTGGGACGAGACTTACTGG

GGCCAAGGGACTCTGGTCACTGTCTCTGCAGCCAAAACGACACCCCCATCGTCTATCCACTG

Variable part heavy chain protein sequence
(SEQ ID NO: 56)
MGWSGVFIFLLSGTAGVHSEVQLQQSGPELVKPGASMKISCKASGYSFTGYTMNWVKQSH

GKNLEWIGLINPYNGVTRYNQKFKGKATLIVDKSSSTAYMELLSLTSEDSAVYYCTREAK

REWDETYWGQGTLVTVSAAKTTPPSVYPL 2.7.3 Clone 17-4-3
Variable part light chain, nucleotide sequence
(SEQ ID NO: 57)
ATGAAGTTGCCTGTTAGGCTGTTGGTGCTGGTGTTCTGGATTCCTGTTTCCAGCAGTGATGTTG

TGATGACCCAGACTCCACTCTCCCTGCCTGTCAGTCTTGGAGATCAAGCCTCCATCTCTTGCAG

ATCTAGTCAGAGCCTTGTACACAGTGATGGAAACACCTATTTACATTGGTACCTGCAGAAGCCA

GGCCAGTCTCCAAAGCTCCTGATCTACAAAGTTTCCAACCGATTTTCTGGGGTCCCAGACAGGT

TCAGTGGCAGTGGATCAGGGACAGATTTCACACTCAAGATCAGCAGAGTGGAGGCTGAGGATCT

GGGAGTTTATTTCTGCTCTCAAAGTACACATGTTCCTCCGACGTTCGGTGGAGGCACCAAGCTG

GAAATCAAACGGGCTGATGCTGCACCAACTGTATCCATCTTCCCACCATCCAGT

Variable part light chain protein sequence
(SEQ ID NO: 58)
MKLPVRLLVLVFWIPVSSSDVVMTQTPLSLPVSLGDQASISCRSSQSLVHSDGNTYLHWY

LQKPGQSPKLLIYKVSNRFSGVPDRFSGSGSGTDFTLKISRVEAEDLGVYFCSQSTHVPP

TFGGGTKLEIKRADAAPTVSIFPPSS

Variable part heavy chain nucleotide sequence
(SEQ ID NO: 59)
ATGGACTTTGGGCTCAGCTTACTTATTTTTGTCCTTATTTTAAAAGGTGTCCAGTGTGAG

GTGAAGCTGGTGGAGTCTGGGGGAGGCTTAGTGCAGCCTGGAGGGTCCCGGAAACTCTCC

TGTGCAGCCTCTGGATTCACTTTCAGTGACTACGGAATGGCGTGGGTTCGACAGGCTCCA

GGGAAGGGGCCTGAGTGGGTAGCATTCATTAGTAATTTGGCATATAGTATCTACTATGCA

GACACTGTGACGGGCCGATTCACCATCTCTAGAGAGAATGCCAAGAACACCCTGTACCTG

GAAATGAGCAGTCTGAGGTCTGAGGACACAGCCATGTACTACTGTGCAAGGTATGACTAC

GATAATATCTTGGACTATGTTATGGACTACTGGGGTCAAGGAACCTCAGTCACCGTCTCC

TCAGCCAAAACAACACCCCCATCAGTCTATCCACTG

Variable part heavy chain protein sequence
(SEQ ID NO: 60)
MDFGLSLLIFVLILKGVQCEVKLVESGGGLVQPGGSRKLSCAASGFTFSDYGMAWVRQAP

GKGPEWVAFISNLAYSIYYADTVTGRFTISRENAKNTLYLEMSSLRSEDTAMYYCARYDY

DNILDYVMDYWGQGTSVTVSSAKTTPPSVYPL 2.7.4 Clone 24-2-3
Variable part light chain nucleotide sequence
(SEQ ID NO: 61)
ATGAAGTTGCCTGTTAGGCTGTTGGTGCTCTGGATTCAGGAAACCAAGGGTGATGTTGTGCTGA

CCCAGACTCCACTCACTTTGTCGGTTACCATTGGACAACCAGCCTCTATCTCTTGCAAGTCAAG

TCAGAGCCTCTTATATAGTAATGGAAAAACCTATTTGAATTGGTTATTACAGAGGCCAGGCCAG

TCTCCAAAGCGCCTAATCTATGTGGTGTCTAAACTGGACTCTGGAGTCCCTGACAGGTTCACTG

GCAGTGGATCAGGAACAGATTTTACACTGAAAATCAGCAGAGTGGAGGCTGAGGATTTGGGAGT

TTATTATTGCGTGCAAGGTACACATTTTCCATTCACGTTCGGCTCGGGGACAAAGTTGGAAATA

AAACGGGCTGATGCTGCACCAACTGTATCCATCTTCCCACCATCCAGT

Variable part light chain protein sequence
(SEQ ID NO: 62)
MKLPVRLLVLWIQETKGDVVLTQTPLTLSVTIGQPASISCKSSQSLLYSNGKTYLNWLLQ

RPGQSPKRLIYVVSKLDSGVPDRFTGSGSGTDFTLKISRVEAEDLGVYYCVQGTHFPFTF

GSGTKLEIKRADAAPTVSIFPPSS

Variable part heavy chain nucleotide sequence
(SEQ ID NO: 63)
ATGGGATGGAGCGGGGTCTTTCTCTTCCTCCTGTCAGTAACTGAAGGTGTCCACTCCCAGGTTC

AGCTGCAGCAGTCTGGGGCTGAGCTGGTGAGGCCTGGGTCCTCAGTGAAGATTTCCTGCAAGGC

TTCTGGCTATATATTCAATAACTACTGGATAAACTGGGTGAAGCAGAGGCCTGGTCAGGGTCTT

GAGTGGATTGGACAGATTTATCCTGGAGATGGTGATACTAACTACAATGGGAAGTTCAAGGGTA

AAGCCACACTGACTGCAGACAAATCCTCCAGCACAGCCTACATGCAGCTCAGCAGCCTAACATC

TGAGGACTCTGCGGTCTATTTCTGTGCAAGAGAGGGATATATTGTTTATTGGGGCCAAGGGACT

CTGGTCACTGTCTCTGCAGCCAAAACGACACCCCCATCTGTCTATCCACTG

Variable part heavy chain protein sequence
(SEQ ID NO: 64)
MGWSGVFLFLLSVTEGVHSQVQLQQSGAELVRPGSSVKISCKASGYIFNNYWINWVKQRP

GQGLEWIGQIYPGDGDTNYNGKFKGKATLTADKSSSTAYMQLSSLTSEDSAVYFCAREGY

Figure 8:
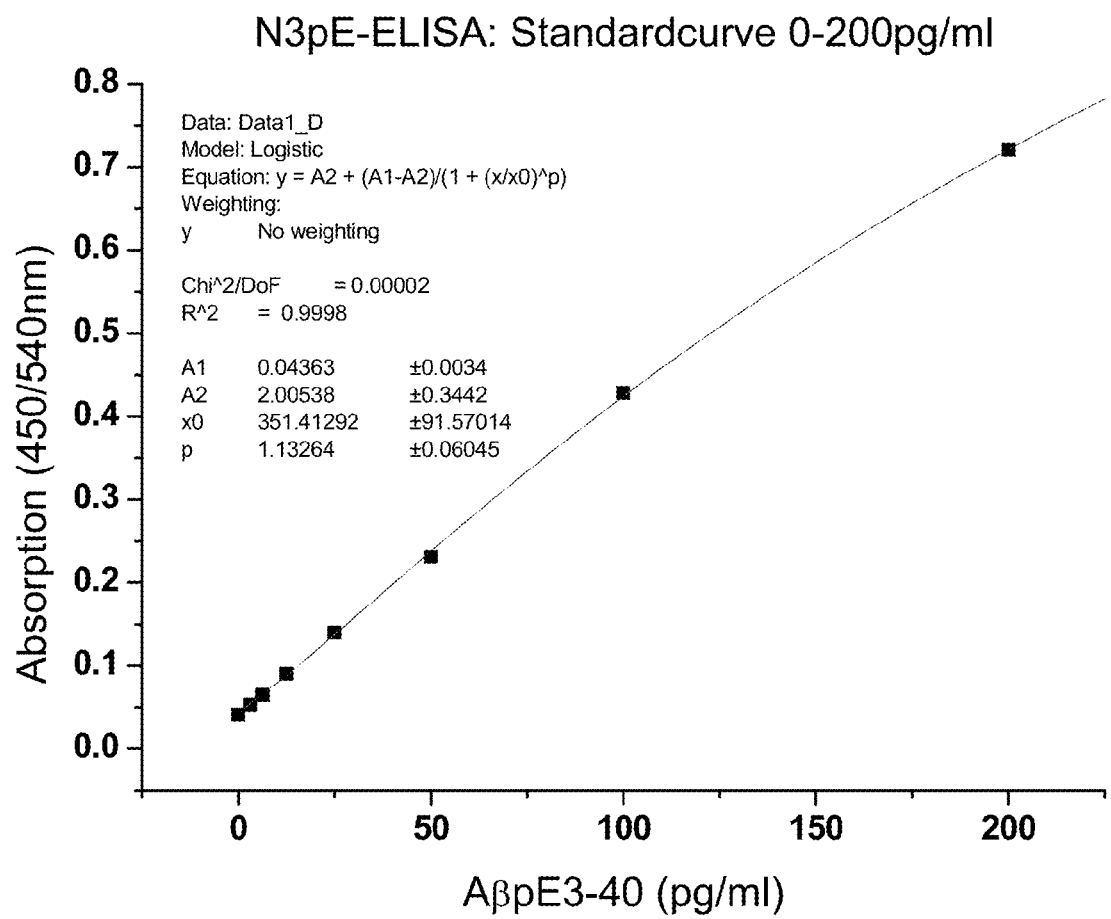

IVYWGQGTLVTVSAAKTTPPSVYPL 2.8 Application of Antibody Clone 6-1-6 for N3pE ELISA The final N3pE ELISA protocol was tested concerning limit of quantification (LOQ) and signal-to-noise ratio (S/N). The standard curve of the ELISA is shown in FIG. 8.

The shape of the standard curve looks very good especially for the low concentration range, which shows a nearly linear dependency of the absorbance. Based on this standard curve the LOQ is determined with 3.125 µg/ml with a S/N=1.3.

2.9 Investigation of Cross Reactivity, Analyzed Via ELISA and SPR

ELISA:

The cross reactivity to other Aβ variants was determined using our N3pE-ELISA. The raw date are shown in table 4.

TABLE 4

Raw date of N3pE-ELISA with clone 6-1-6:
Test of cross reactivity

| Concentration (pg/ml) | pE3-40 (28.04.) | pE3-40 (21.04.) | 2-40 | 3-40 | 4-40 | 1-42 | 3-42 | pE11-40 |
|---|---|---|---|---|---|---|---|---|
| 800 | 1.8280 | 1.806 | 0.048 | 0.090 | 0.055 | 0.053 | 0.052 | 0.047 |
| 400 | 0.8750 | 0.912 | 0.045 | 0.065 | 0.044 | 0.048 | 0.052 | 0.044 |
| 200 | 0.4350 | 0.484 | 0.044 | 0.057 | 0.046 | 0.048 | 0.049 | 0.048 |
| 100 | 0.2290 | 0.248 | 0.045 | 0.052 | 0.045 | 0.047 | 0.050 | 0.048 |
| 50 | 0.1330 | 0.143 | 0.044 | 0.048 | 0.044 | 0.050 | 0.045 | 0.045 |
| 25 | 0.0820 | 0.086 | 0.044 | 0.046 | 0.044 | 0.048 | 0.047 | 0.048 |
| 12.5 | 0.0570 | 0.063 | 0.039 | 0.042 | 0.040 | 0.043 | 0.042 | 0.046 |
| 0 | 0.0410 | 0.040 | 0.038 | 0.065 | 0.061 | 0.059 | 0.063 | 0.066 |

Only for AβpE3-40 a dependency of the absorbance from the concentration was observed. All tested Aβ variants have shown cross reactivity below 1%, except of 4β3-40. The signal (corrected by the blank) for 800 pg/ml was about 2.7% of the signal for AβpE3-40. This is a very good value, considering that the N-terminus of both peptides have the same amino acids, except the first one, this is cyclized in the case of AβpE3-40. Overall, the Aβ N3pE antibody clone 6, which is generally used for ELISA, is very high specific for the N-terminus of Aβ-peptides starting with pGlu at position 3.

Figure 9:
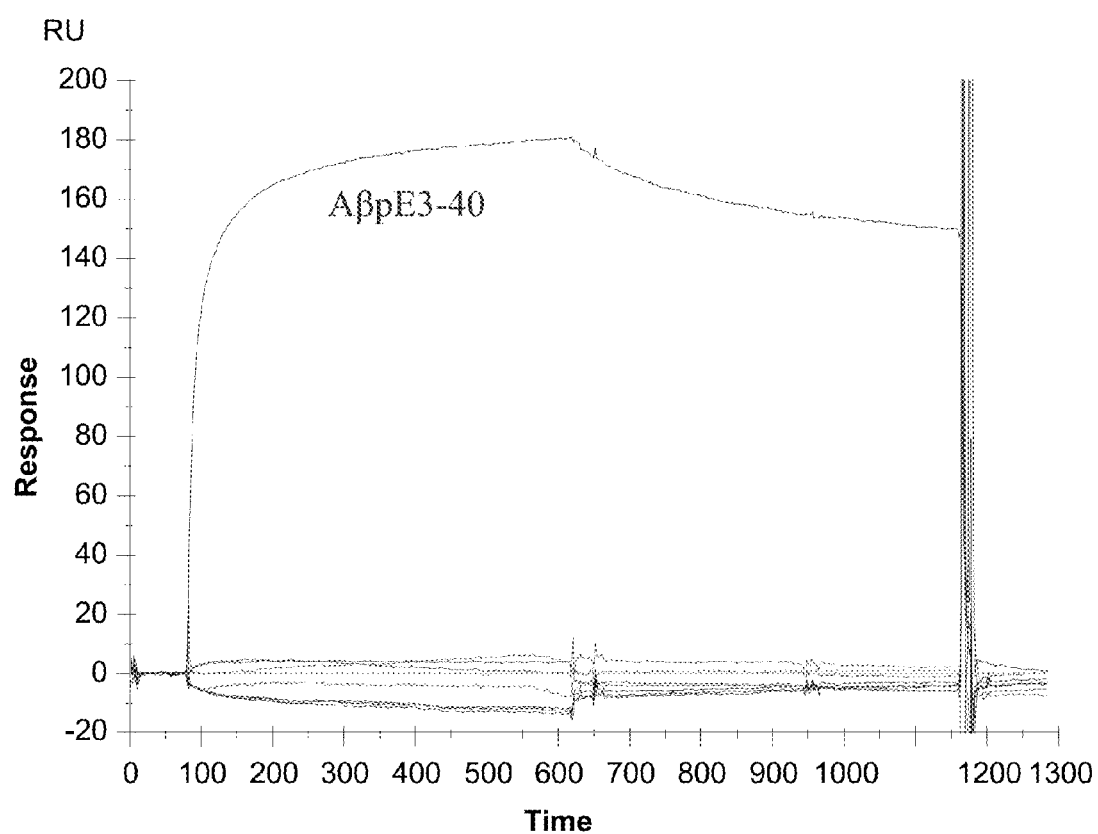

SPR:

The cross reactivity of clones 6-1-6 and 24-2-3 to other non-Aβ pGlu peptides was analyzed by surface plasmon resonance. Instead of AβpE3-40, which shows a typical binding sensogram, all other tested pGlu peptides have shown nearly no interaction with clones 6-1-6 and 24-2-3, respectively, see also FIG. 9 (data only shown for clone 6-1-6). The sensograms of the pGlu peptides were compared with the sensogram for AβpE3-40. The estimated cross reactivities were all below 1%. A summary of all analyzed peptides are shown in table 5.

TABLE 5

Estimated Cross reactivity of clones 6-1-6 and 24-2-3 to other pGlu-peptides

| pGlu Peptides | % cross reactivity |
|---|---|
| MCP-1 | <1 |
| MCP-2 | <1 |
| Big Gastrin | <1 |
| Gonadoliberin | <1 |
| Neurotensin | <1 |
| Orexin A | <1 |
| Fibronectin | <1 |
| Collagen 1 | <1 |
| TRH | <1 |

All experiments have confirmed the fact that N3pE antibody clone 6-1-6 and 24-2-3 are specific for the N-terminal epitope of AβpE3-x. Neither other pGlu N-termini were recognized nor other Aβ peptide variants, which do not bear an N-terminal pE residue.

2.10 Optimization and Validation of N3pE ELISA for Brain Analysis

AβpE3-42 concentration in mouse brainstem was analyzed dependent on the used method. The samples were derived from transgenic mice (tg) overexpressing human AβQ3-42 in the brain, which is cyclized by QC to AβpE3-42. Compared were samples from heterozygous transgenic mice (tg het) and homozygous transgenic mice (tg hom) and from wildtype, non-transgenic mice (wt). The mice used for sample generation were produced as described in WO2009034158.

Figure 10:
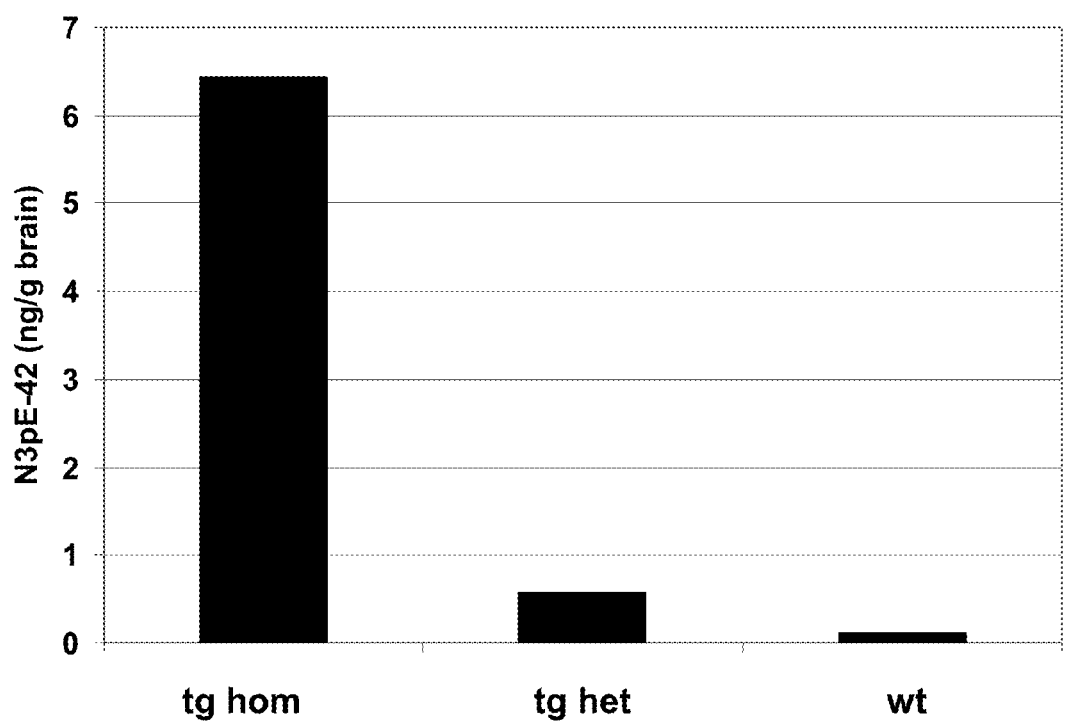

For all further experiments samples and standards were diluted in the EIA buffer. In a next step, the neutralization method for analyzing formic acid fraction samples was optimized, i.e. the neutralization was N3pE ELISA. The resulting and herein developed N3pE ELISA works well, it detected significant levels of human AβpE3-42 in brains of the tg hom mice, significantly lower levels of human AβpE3-42 in brains of the tg het mice and no human AβpE3-42 in brains of the wt mice (see FIG. 10). The ELISA according to the present invention delivers high signals and consequently a very acceptable LOQ and is thus suitable for analysis of formic acid samples, in particular of formic acid brain samples.

2.11 Application of N3pE Antibody Clones for Immunohistochemistry

With the N3pE antibodies of the present invention, AβpE3-x was stained in brain sections of patients in the late stage of sporadic Alzheimer's disease (SAD) and familial forms of Alzheimer's disease (FAD), i.e. patients which bear a mutation in the presenilin 1 (PS1) gene. The stained brain sections are shown in FIG. 11. FIG. 11 shows that the N3pE antibodies of the present invention are suitable for immunohistochemistry. The antibodies specifically detect pGlu-Aβ in brain of SAD and FAD patients. The N3pE antibodies show no background signals on the images, which proves the specific binding shown by ELISA and SPR analysis.

3. Deposits

Monoclonal antibodies specifically recognizing Aβ N3pE-x, were generated. Currently all corresponding monoclonal antibodies expressing hybridoma cell lines 5-5-6, 6-1-6, 17-4-3, and 24-2-3 have been deposited in accordance with the Budapest Treaty and are available at the Deutsche Sammlung für Mikroorganismen and Zellkulturen (DSMZ) in Braunschweig, DE, with a deposit date of Jun. 17, 2008, and with the respective deposit numbers (clone 5-5-6) DSM ACC2923
(clone 6-1-6) DSM ACC2924
(clone 17-4-3) DSM ACC2925
(clone 24-2-3) DSM ACC2926.

Specificity of those antibodies for their respective target sequences could be confirmed. For Aβ N3pE-x, high affinity antibody clones could be identified that should give strong signals in an ELISA set up with an expected detection limit in the low pg range.

4. Summary

One objective of the present invention was the establishment of a highly sensitive and robust detection technique that allows quantitative determination of Aβ variants in biological samples.

Preferably, an ELISA based technique can be pursued. The task was started with Aβ N3pE ELISA, because for this Aβ variant an appropriate ELISA system was already commercially available (IBL). This system was used as reference and internal quality control.

Applicability of the pGlu-6166 antibody in the chosen ELISA assay set up was investigated. To obtain clearly measurable signals, high antibody concentrations needed to be deployed (20 µg/ml). High affinity Aβ N3pE-x antibody clones could be identified. A detection limit in the low pg range (3-8 µg/ml) can be achieved with these clones.

The invention claimed is:

1. A method for treatment or delay of an amyloid beta-associated amyloidosis comprising administering a therapeutically effective amount of an antibody or a humanized form of said antibody to a subject in need thereof, wherein the antibody comprises
   (i) a light chain comprising a variable part, the variable part of the light chain of said antibody comprising a polypeptide
      (a) encoded by a nucleotide sequence selected from the group consisting of SEQ ID NO: 49, SEQ ID NO: 53, SEQ ID NO: 57, and SEQ ID NO: 61 or
      (b) having an amino acid sequence selected from the group consisting of SEQ ID NO: 50, SEQ ID NO: 54, SEQ ID NO: 58, and SEQ ID NO: 62; or
   (ii) a heavy chain comprising a variable part; the variable part of the heavy chain of said antibody comprising a polypeptide
      (a) encoded by a nucleotide sequence selected from the group consisting of SEQ ID NO: 51, SEQ ID NO: 55, SEQ ID NO: 59, and SEQ ID NO: 63 or
      (b) having an amino acid sequence selected from the group consisting of SEQ ID NO: 52, SEQ ID NO: 56, SEQ ID NO: 60, and SEQ ID NO: 64.

2. The method of claim 1, wherein said amyloidosis is a neurodegenerative disease selected from the group consisting of mild cognitive impairment, Alzheimer's disease and neurodegeneration in Down Syndrome.

3. The method of claim 1, wherein said amyloidosis is sporadic Alzheimer's disease or a Familial Alzheimer's dementia.

4. The method of claim 3, wherein said Familial Alzheimer's dementia is Familial British Dementia or Familial Danish Dementia.

5. The method according to claim 1, wherein the antibody binds an Aβ peptide with a dissociation constant (KD) value of at least $10^{-7}$ M.

6. The method according to claim 1, wherein said antibody is a monoclonal antibody.

7. The method according to claim 1, wherein:
the antibody comprises the light chain;
the light chain comprises the variable part; and
the variable part of the light chain of said antibody comprises the polypeptide encoded by the nucleotide sequence selected from the group consisting of SEQ ID NO: 49, SEQ ID NO: 53, SEQ ID NO: 57 and SEQ ID NO: 61, or having the amino acid sequence selected from the group consisting of SEQ ID NO: 50, SEQ ID NO: 54, SEQ ID NO: 58, and SEQ ID NO: 62.

8. The method according to claim 1, wherein:
the antibody comprises the heavy chain;
the heavy chain comprises the variable part; and
the variable part of the heavy chain of said antibody comprises the polypeptide encoded by the nucleotide sequence selected from SEQ ID NO: 51, SEQ ID NO: 55, SEQ ID NO: 59 and SEQ ID NO: 63, or having the amino acid sequence selected from SEQ ID NO: 52, SEQ ID NO: 56, SEQ ID NO: 60 and SEQ ID NO: 64.

9. The method according to claim 1, wherein:
the isolated antibody comprises the light chain;
the light chain comprises the variable part;
the variable part of the light chain of said antibody comprises the polypeptide encoded by the nucleotide sequence of SEQ ID NO: 49 or having the amino acid sequence of SEQ ID NO: 50;
the isolated antibody comprises the heavy chain;
the heavy chain comprises the variable part; and
the variable part of the heavy chain of said antibody comprises the polypeptide encoded by the nucleotide sequence of SEQ ID NO: 51, or having the amino acid sequence of SEQ ID NO: 52.

10. The method according to claim 1, wherein:
the isolated antibody comprises the light chain;
the light chain comprises the variable part;
the variable part of the light chain of said antibody comprises the polypeptide encoded by the nucleotide sequence of SEQ ID NO: 53 or having the amino acid sequence of SEQ ID NO: 54;
the isolated antibody comprises the heavy chain;
the heavy chain comprises the variable part; and
the variable part of the heavy chain of said antibody comprises the polypeptide encoded by the nucleotide sequence of SEQ ID NO: 55, or having the amino acid sequence of SEQ ID NO: 56.

11. The method according to claim 1, wherein:
the isolated antibody comprises the light chain;
the light chain comprises the variable part;
the variable part of the light chain of said antibody comprises the polypeptide encoded by the nucleotide sequence of SEQ ID NO: 57 or having the amino acid sequence of SEQ ID NO: 58;
the isolated antibody comprises the heavy chain;
the heavy chain comprises the variable part; and
the variable part of the heavy chain of said antibody comprises the polypeptide encoded by the nucleotide sequence of SEQ ID NO: 59, or having the amino acid sequence of SEQ ID NO: 60.

12. The method according to claim 1, wherein:
the isolated antibody comprises the light chain;
the light chain comprises the variable part;
the variable part of the light chain of said antibody comprises the polypeptide encoded by the nucleotide sequence of SEQ ID NO: 61 or having the amino acid sequence of SEQ ID NO: 62;
the isolated antibody comprises the heavy chain;
the heavy chain comprises the variable part; and
a polypeptide encoded by the nucleotide sequence of SEQ ID NO: 63, or having the amino acid sequence of SEQ ID NO: 64.

13. The method according to claim 1, wherein said antibody is selected from the group consisting of:
Aβ 5-5-6 (Deposit No. DSM ACC 2923);
Aβ 6-1-6 (Deposit No. DSM ACC 2924);

Aβ 17-4-3 (Deposit No. DSM ACC 2925); and
Aβ 24-2-3 (Deposit No. DSM ACC 2926).

14. The method according to claim 1, wherein said antibody is Aβ 6-1-6 (Deposit No. DSM ACC 2924).

15. The method according to claim 1, wherein said antibody is Aβ 24-2-3 (Deposit No. DSM ACC 2926).

16. The method according to claim 1, wherein said antibody is a humanized or chimeric antibody, or an antibody fragment.

17. The method according to claim 1, wherein the antibody is a human antibody other than the variable part of the light chain and the variable part of the heavy chain.

18. The method according to claim 1, wherein the antibody is a diabody or a single chain antibody.

19. The method according to claim 1, wherein the antibody binds to an epitope of an antigen selected from the group consisting of:
pGlu-Aβ3-38;
pGlu-Aβ3-40;
pGlu-Aβ3-42; and
pGlu-Aβ3-x variants,
wherein x is an integer between 10 and 42.

20. The method according to claim 1, wherein the antibody comprises a complementarity determining region that binds to an antigen selected from the group consisting of:
pGlu-Aβ3-38;
pGlu-Aβ3-40;
pGlu-Aβ3-42; and
pGlu-Aβ3-x variants,
wherein x is an integer between 10 and 42.

21. The method according to claim 1, wherein the antibody is labeled.

22. The method according to claim 1, wherein the antibody is obtained from any one of hybridoma cell lines DSM ACC 2923, DSM ACC 2924, DSM ACC 2925, or DSM ACC 2926.

23. The method according to claim 19, wherein x is an integer between 18 and 42.

24. The method according to claim 19, wherein x is an integer between 30 and 42.

25. The method according to claim 20, wherein x is an integer between 18 and 42.

26. The method according to claim 20, wherein x is an integer between 30 and 42.

* * * * *

SEQUENCE LISTING

<160> NUMBER OF SEQ ID NOS: 65

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
            35                  40

<210> SEQ ID NO 3
<211> LENGTH: 38
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly
            35

<210> SEQ ID NO 4
<211> LENGTH: 40
<212> TYPE: PRT
<213> ORGANISM: Homo sapiens

<400> SEQUENCE: 4

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
            35                  40

<210> SEQ ID NO 5
<211> LENGTH: 38
<212> TYPE: PRT
<213> ORGANISM: Homo sapiens

<400> SEQUENCE: 5

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
            35

<210> SEQ ID NO 6
<211> LENGTH: 36
<212> TYPE: PRT

<213> ORGANISM: Homo sapiens

<400> SEQUENCE: 6

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly
            35

<210> SEQ ID NO 7
<211> LENGTH: 13
<212> TYPE: PRT
<213> ORGANISM: Homo sapiens

<400> SEQUENCE: 7

Lys Met Asp Ala Glu Phe Arg His Asp Ser Gly Tyr Glu
1               5                   10

<210> SEQ ID NO 8
<211> LENGTH: 13
<212> TYPE: PRT
<213> ORGANISM: Homo sapiens

<400> SEQUENCE: 8

Asp Ala Glu Phe Arg His Asp Ser Gly Tyr Glu Val His
1               5                   10

<210> SEQ ID NO 9
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Isoaspartate

<400> SEQUENCE: 9

Asp Ala Glu Phe Arg His Asp Ser Gly Tyr Glu Val His
1               5                   10

<210> SEQ ID NO 10
<211> LENGTH: 13
<212> TYPE: PRT
<213> ORGANISM: Homo sapiens

<400> SEQUENCE: 10

Ala Glu Phe Arg His Asp Ser Gly Tyr Glu Val His His
1               5                   10

<210> SEQ ID NO 11
<211> LENGTH: 13
<212> TYPE: PRT
<213> ORGANISM: Homo sapiens

<400> SEQUENCE: 11

Glu Phe Arg His Asp Ser Gly Tyr Glu Val His His Gln
1               5                   10

<210> SEQ ID NO 12
<211> LENGTH: 13
<212> TYPE: PRT
<213> ORGANISM: Homo sapiens
<220> FEATURE:
<221> NAME/KEY: MISC_FEATURE

```
<222> LOCATION: (1)..(1)
<223> OTHER INFORMATION: pyroglutamate

<400> SEQUENCE: 12

Glu Phe Arg His Asp Ser Gly Tyr Glu Val His His Gln
1               5                   10

<210> SEQ ID NO 13
<211> LENGTH: 13
<212> TYPE: PRT
<213> ORGANISM: Homo sapiens

<400> SEQUENCE: 13

Phe Arg His Asp Ser Gly Tyr Glu Val His His Gln Lys
1               5                   10

<210> SEQ ID NO 14
<211> LENGTH: 13
<212> TYPE: PRT
<213> ORGANISM: Homo sapiens

<400> SEQUENCE: 14

Gly Tyr Glu Val His His Gln Lys Leu Val Phe Phe Ala
1               5                   10

<210> SEQ ID NO 15
<211> LENGTH: 13
<212> TYPE: PRT
<213> ORGANISM: Homo sapiens

<400> SEQUENCE: 15

Glu Val His His Gln Lys Leu Val Phe Phe Ala Glu Asp
1               5                   10

<210> SEQ ID NO 16
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: pyroglutamate

<400> SEQUENCE: 16

Glu Val His His Gln Lys Leu Val Phe Phe Ala Glu Asp
1               5                   10

<210> SEQ ID NO 17
<211> LENGTH: 13
<212> TYPE: PRT
<213> ORGANISM: Homo sapiens

<400> SEQUENCE: 17

Val His His Gln Lys Leu Val Phe Phe Ala Glu Asp Val
1               5                   10

<210> SEQ ID NO 18
<211> LENGTH: 13
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: isoaspartate

<400> SEQUENCE: 18
```

Asp Ala Glu Phe Arg His Asp Ser Gly Tyr Glu Val His
1               5                   10

<210> SEQ ID NO 19
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: isoaspartate

<400> SEQUENCE: 19

Asp Ser Gly Tyr Glu Val His His Gln Lys Leu Val Phe
1               5                   10

<210> SEQ ID NO 20
<211> LENGTH: 13
<212> TYPE: PRT
<213> ORGANISM: Homo sapiens

<400> SEQUENCE: 20

Leu Val Phe Phe Ala Glu Asp Val Gly Ser Asn Lys Gly
1               5                   10

<210> SEQ ID NO 21
<211> LENGTH: 13
<212> TYPE: PRT
<213> ORGANISM: Homo sapiens

<400> SEQUENCE: 21

Gly Ser Asn Lys Gly Ala Ile Ile Gly Leu Met Val Gly
1               5                   10

<210> SEQ ID NO 22
<211> LENGTH: 11
<212> TYPE: PRT
<213> ORGANISM: Homo sapiens

<400> SEQUENCE: 22

Ala Ile Ile Gly Leu Met Val Gly Gly Val Val
1               5                   10

<210> SEQ ID NO 23
<211> LENGTH: 30
<212> TYPE: DNA
<213> ORGANISM: Artificial sequence
<220> FEATURE:
<223> OTHER INFORMATION: PCR primer

<400> SEQUENCE: 23
atgaagttgc ctgttaggct gttggtgctg                                    30

<210> SEQ ID NO 24
<211> LENGTH: 30
<212> TYPE: DNA
<213> ORGANISM: Artificial sequence
<220> FEATURE:
<223> OTHER INFORMATION: PCR primer

<400> SEQUENCE: 24
atggagwcag acacactcct gytatgggtg                                    30

<210> SEQ ID NO 25
<211> LENGTH: 30
<212> TYPE: DNA

```
<213> ORGANISM: Artificial sequence
<220> FEATURE:
<223> OTHER INFORMATION: PCR primer

<400> SEQUENCE: 25
atgagtgtgc tcactcaggt cctggsgttg                                    30

<210> SEQ ID NO 26
<211> LENGTH: 33
<212> TYPE: DNA
<213> ORGANISM: Artificial sequence
<220> FEATURE:
<223> OTHER INFORMATION: PCR primer

<400> SEQUENCE: 26
atgaggrccc ctgctcagwt tyttggmwtc ttg                                33

<210> SEQ ID NO 27
<211> LENGTH: 30
<212> TYPE: DNA
<213> ORGANISM: Artificial sequence
<220> FEATURE:
<223> OTHER INFORMATION: PCR primer

<400> SEQUENCE: 27
atggatttwc aggtgcagat twtcagcttc                                    30

<210> SEQ ID NO 28
<211> LENGTH: 27
<212> TYPE: DNA
<213> ORGANISM: Artificial sequence
<220> FEATURE:
<223> OTHER INFORMATION: PCR primer

<400> SEQUENCE: 28
atgaggtkcy ytgytsagyt yctgrgg                                       27

<210> SEQ ID NO 29
<211> LENGTH: 31
<212> TYPE: DNA
<213> ORGANISM: Artificial sequence
<220> FEATURE:
<223> OTHER INFORMATION: PCR primer

<400> SEQUENCE: 29
atgggcwtca agatggagtc acakwyycwg g                                  31

<210> SEQ ID NO 30
<211> LENGTH: 31
<212> TYPE: DNA
<213> ORGANISM: Artificial sequne
<220> FEATURE:
<223> OTHER INFORMATION: PCR primer

<400> SEQUENCE: 30 atgtgggay ctktttycmm tttttcaatt g                                   31

<210> SEQ ID NO 31
<211> LENGTH: 25
<212> TYPE: DNA
<213> ORGANISM: Artificial sequence
<220> FEATURE:
<223> OTHER INFORMATION: PCR primer

<400> SEQUENCE: 31
atggtrtccw casctcagtt ccttg                                         25
```

<210> SEQ ID NO 32
<211> LENGTH: 27
<212> TYPE: DNA
<213> ORGANISM: Artificial sequence
<220> FEATURE:
<223> OTHER INFORMATION: PCR primer

<400> SEQUENCE: 32
atgtatatat gtttgttgtc tatttct                                27

<210> SEQ ID NO 33
<211> LENGTH: 28
<212> TYPE: DNA
<213> ORGANISM: Artificial sequence
<220> FEATURE:
<223> OTHER INFORMATION: PCR primer

<400> SEQUENCE: 33
atggaagccc cagctcagct tctcttcc                               28

<210> SEQ ID NO 34
<211> LENGTH: 20
<212> TYPE: DNA
<213> ORGANISM: Artificial sequence
<220> FEATURE:
<223> OTHER INFORMATION: PCR primer

<400> SEQUENCE: 34
actggatggt gggaagatgg                                        20

<210> SEQ ID NO 35
<211> LENGTH: 27
<212> TYPE: DNA
<213> ORGANISM: Artificial sequence
<220> FEATURE:
<223> OTHER INFORMATION: PCR primer

<400> SEQUENCE: 35
atgaaatgca gctggggcat sttcttc                                27

<210> SEQ ID NO 36
<211> LENGTH: 26
<212> TYPE: DNA
<213> ORGANISM: Artificial sequence
<220> FEATURE:
<223> OTHER INFORMATION: PCR primer

<400> SEQUENCE: 36
atgggatgga gctrtatcat sytctt                                 26

<210> SEQ ID NO 37
<211> LENGTH: 27
<212> TYPE: DNA
<213> ORGANISM: Artificial sequence
<220> FEATURE:
<223> OTHER INFORMATION: PCR primer

<400> SEQUENCE: 37
atgaagwtgt ggttaaactg ggtttt                                 27

<210> SEQ ID NO 38
<211> LENGTH: 25
<212> TYPE: DNA
<213> ORGANISM: Artificial sequence
<220> FEATURE:

```
<223> OTHER INFORMATION: PCR primer

<400> SEQUENCE: 38
atgractttg ggytcagctt grttt                                           25

<210> SEQ ID NO 39
<211> LENGTH: 30
<212> TYPE: DNA
<213> ORGANISM: Artificial sequence
<220> FEATURE:
<223> OTHER INFORMATION: PCR primer

<400> SEQUENCE: 39
atggactcca ggctcaattt agttttcctt                                      30

<210> SEQ ID NO 40
<211> LENGTH: 28
<212> TYPE: DNA
<213> ORGANISM: Artificial sequence
<220> FEATURE:
<223> OTHER INFORMATION: PCR primer

<400> SEQUENCE: 40
atggcttgtc ytrgsgctrc tcttctgc                                        28

<210> SEQ ID NO 41
<211> LENGTH: 26
<212> TYPE: DNA
<213> ORGANISM: Artificial sequence
<220> FEATURE:
<223> OTHER INFORMATION: PCR primer

<400> SEQUENCE: 41
atggratgga gckggrtctt tmtctt                                          26

<210> SEQ ID NO 42
<211> LENGTH: 23
<212> TYPE: DNA
<213> ORGANISM: Artificial sequence
<220> FEATURE:
<223> OTHER INFORMATION: PCR primer

<400> SEQUENCE: 42
atgagagtgc tgattctttt gtg                                             23

<210> SEQ ID NO 43
<211> LENGTH: 30
<212> TYPE: DNA
<213> ORGANISM: Artificial sequence
<220> FEATURE:
<223> OTHER INFORMATION: PCR primer

<400> SEQUENCE: 43
atggmttggg tgtggamctt gctattcctg                                      30

<210> SEQ ID NO 44
<211> LENGTH: 27
<212> TYPE: DNA
<213> ORGANISM: Artificial sequence
<220> FEATURE:
<223> OTHER INFORMATION: PCR primer

<400> SEQUENCE: 44
atgggcagac ttacattctc attcctg                                         27
```

```
<210> SEQ ID NO 45
<211> LENGTH: 28
<212> TYPE: DNA
<213> ORGANISM: Artificial sequence
<220> FEATURE:
<223> OTHER INFORMATION: PCR primer

<400> SEQUENCE: 45
atggattttg ggctgatttt ttttattg                                      28

<210> SEQ ID NO 46
<211> LENGTH: 27
<212> TYPE: DNA
<213> ORGANISM: Artificial sequence
<220> FEATURE:
<223> OTHER INFORMATION: PCR primer

<400> SEQUENCE: 46
atgatggtgt taagtcttct gtacctg                                       27

<210> SEQ ID NO 47
<211> LENGTH: 21
<212> TYPE: DNA
<213> ORGANISM: Artificial sequence
<220> FEATURE:
<223> OTHER INFORMATION: PCR primer

<400> SEQUENCE: 47
cagtggatag acagatgggg g                                             21

<210> SEQ ID NO 48
<211> LENGTH: 21
<212> TYPE: DNA
<213> ORGANISM: Artificial sequence
<220> FEATURE:
<223> OTHER INFORMATION: PCR primer

<400> SEQUENCE: 48
cagtggatag actgatgggg g                                             21

<210> SEQ ID NO 49
<211> LENGTH: 436
<212> TYPE: DNA
<213> ORGANISM: Mus musculus

<400> SEQUENCE: 49
atggtgtcct cagctcagtt cctgtttctg ttagtgctct ggattcagga aaccaacggt    60
gatgttgtga tgacccagac tccactcact ttgtcggtta ccattggaca accagcctct   120
atctcttgca agtcaagtca gagcctctta tatagtgatg gaaaaaccta tttgaattgg   180
ttattacaga ggccaggcca gtctccaatg cgcctaatct atctggtgtc taaactggac   240
tctggagtcc ctgacaggtt cactggcagt ggatcaggaa cagattttac actgaaaatc   300
agcagagtgg aggctgagga tttgggagtt tattactgcg tgcaaggtac acattttcca   360
ttcacgttcg gctcggggac aaagttggaa ataaaacggg ctgatgctgc accaactgta   420
tccatcttcc caccat                                                   436

<210> SEQ ID NO 50
<211> LENGTH: 145
<212> TYPE: PRT
<213> ORGANISM: Mus musculus

<400> SEQUENCE: 50
```

Met Val Ser Ser Ala Gln Phe Leu Phe Leu Leu Val Leu Trp Ile Gln
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Tyr Ser Asp Gly Lys Thr Tyr Leu Asn Trp Leu Leu Gln Arg
    50                  55                  60

Pro Gly Gln Ser Pro Met Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Val Gln Gly Thr His Phe Pro Phe Thr Phe Gly Ser Gly Thr Lys
        115                 120                 125

Leu Glu Ile Lys Arg Ala Asp Ala Ala Pro Thr Val Ser Ile Phe Pro
    130                 135                 140

Pro
145

<210> SEQ ID NO 51
<211> LENGTH: 440
<212> TYPE: DNA
<213> ORGANISM: Mus musculus

<400> SEQUENCE: 51
atgggatgga gcggggtctt tctcttcctc ctgtcaggaa ctgcaggtgt ccactctgag    60
gtccagctgc aacagtctgg acctgagctg gtgaagcctg agcttcaat gaagatatcc    120
tgcaaggctt ctggttactc attcactggc tataccatga actgggtgaa gcagagccat    180
ggaaagaacc ttgagtggat tggacttatt aatccttaca gtggtgttac taggtacaac    240
cagaaattca gggcaaggc cacattaatt gtagacaagt catccagcac agcctacatg    300
gagctcctca gtctgacatc tgaggactct gcagtctatt attgtacaag agaggctaaa    360
cgggagtggg acgagactta ctggggccaa gggactctgg tcactgtctc tgcagccaaa    420
acgacacccc catctgtcta                                                440

<210> SEQ ID NO 52
<211> LENGTH: 146
<212> TYPE: PRT
<213> ORGANISM: Mus musculus

<400> SEQUENCE: 52

Met Gly Trp Ser Gly Val Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Lys Asn Leu
    50                  55                  60

Glu Trp Ile Gly Leu Ile Asn Pro Tyr Ser Gly Val Thr Arg Tyr Asn
65                  70                  75                  80

Gln Lys Phe Lys Gly Lys Ala Thr Leu Ile Val Asp Lys Ser Ser Ser
                85                  90                  95

Thr Ala Tyr Met Glu Leu Leu Ser Leu Thr Ser Glu Asp Ser Ala Val
                100                 105                 110

Tyr Tyr Cys Thr Arg Glu Ala Lys Arg Glu Trp Asp Glu Thr Tyr Trp
                115                 120                 125

Gly Gln Gly Thr Leu Val Thr Val Ser Ala Ala Lys Thr Thr Pro Pro
        130                 135                 140

Ser Val
145

<210> SEQ ID NO 53
<211> LENGTH: 440
<212> TYPE: DNA
<213> ORGANISM: Mus musculus

<400> SEQUENCE: 53
atggtgtcca cagctcagtt cctgtttctg ttagtgctct ggattcagga aaccaacggt    60
gatgttgtga tgacccagac tccactcact ttgtcggtta ccattggaca accagcctct   120
atctcttgca agtcaagtca gagcctctta tatagtgacg gaaaaaccta tttgaattgg   180
ttattacaga ggccaggcca gtctccaatg cgcctaatct atctggtgtc taaactggac   240
tctggagtcc ctgacaggtt cactggcagt ggatcaggaa cagattttac actgaaaatc   300
agcagagtgg aggctgagga tttgggagtt tattactgcg tgcaaggtac acattttcca   360
ttcacgttcg gctcggggac aaagttggaa ataaaacggg ctgatgctgc accaactgta   420
tccatcttcc caccatccag                                              440

<210> SEQ ID NO 54
<211> LENGTH: 146
<212> TYPE: PRT
<213> ORGANISM: Mus musculus

<400> SEQUENCE: 54

Met Val Ser Thr Ala Gln Phe Leu Phe Leu Leu Val Leu Trp Ile Gln
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Tyr Ser Asp Gly Lys Thr Tyr Leu Asn Trp Leu Leu Gln Arg
    50                  55                  60

Pro Gly Gln Ser Pro Met Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Val Gln Gly Thr His Phe Pro Phe Thr Phe Gly Ser Gly Thr Lys
        115                 120                 125

Leu Glu Ile Lys Arg Ala Asp Ala Ala Pro Thr Val Ser Ile Phe Pro
    130                 135                 140

Pro Ser
145

<210> SEQ ID NO 55
<211> LENGTH: 447
<212> TYPE: DNA

<213> ORGANISM: Mus musculus

<400> SEQUENCE: 55

| | | |
|---|---|---|
| atgggatgga gcggggtctt tatcttcctc ctgtcaggaa ctgcaggtgt ccactctgag | 60 |
| gtccagctgc aacagtctgg acctgagctg gtgaagcctg gagcttcaat gaagatatcc | 120 |
| tgcaaggctt ctggttactc attcactggc tacaccatga actgggtgaa gcagagccat | 180 |
| ggaaagaacc ttgagtggat tggacttatt aatccttaca atggtgttac taggtacaac | 240 |
| cagaagttca aggcaaggc cacattaatt gtagacaagt catccagcac agcctacatg | 300 |
| gagctcctca gtctgacatc tgaggactct gcagtctatt actgtacaag agaggctaaa | 360 |
| cgggagtggg acgagactta ctggggccaa gggactctgg tcactgtctc tgcagccaaa | 420 |
| acgacacccc catctgtcta tccactg | 447 |

<210> SEQ ID NO 56
<211> LENGTH: 149
<212> TYPE: PRT
<213> ORGANISM: Mus musculus

<400> SEQUENCE: 56

Met Gly Trp Ser Gly Val Phe Ile Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Met Asn Trp Val Lys Gln Ser His Gly Lys Asn Leu
    50                  55                  60

Glu Trp Ile Gly Leu Ile Asn Pro Tyr Asn Gly Val Thr Arg Tyr Asn
65                  70                  75                  80

Gln Lys Phe Lys Gly Lys Ala Thr Leu Ile Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Thr Arg Glu Ala Lys Arg Glu Trp Asp Glu Thr Tyr Trp
        115                 120                 125

Gly Gln Gly Thr Leu Val Thr Val Ser Ala Ala Lys Thr Thr Pro Pro
    130                 135                 140

Ser Val Tyr Pro Leu
145

<210> SEQ ID NO 57
<211> LENGTH: 438
<212> TYPE: DNA
<213> ORGANISM: Mus musculus

<400> SEQUENCE: 57

| | | |
|---|---|---|
| atgaagttgc ctgttaggct gttggtgctg gtgttctgga ttcctgtttc cagcagtgat | 60 |
| gttgtgatga cccagactcc actctccctg cctgtcagtc ttggagatca agcctccatc | 120 |
| tcttgcagat ctagtcagag ccttgtacac agtgatggaa acacctattt acattggtac | 180 |
| ctgcagaagc caggccagtc tccaaagctc ctgatctaca agtttccaa ccgattttct | 240 |
| ggggtcccag acaggttcag tggcagtgga tcaggacag atttcacact caagatcagc | 300 |
| agagtggagg ctgaggatct gggagtttat ttctgctctc aaagtacaca tgttcctccg | 360 |
| acgttcggtg gaggcaccaa gctggaaatc aaacgggctg atgctgcacc aactgtatcc | 420 | atcttcccac catccagt 438

<210> SEQ ID NO 58
<211> LENGTH: 146
<212> TYPE: PRT
<213> ORGANISM: Mus musculus

<400> SEQUENCE: 58

Met Lys Leu Pro Val Arg Leu Leu Val Leu Val Phe Trp Ile Pro Val
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asp Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Pro Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser
145

<210> SEQ ID NO 59
<211> LENGTH: 456
<212> TYPE: DNA
<213> ORGANISM: Mus musculus

<400> SEQUENCE: 59
atggactttg ggctcagctt acttattttt gtccttattt taaaaggtgt ccagtgtgag       60
gtgaagctgg tggagtctgg gggaggctta gtgcagcctg agggtcccg gaaactctcc      120 tgtgcagcct ctggattcac tttcagtgac tacggaatgg cgtgggttcg acaggctcca     180
gggaaggggc ctgagtgggt agcattcatt agtaatttgg catatagtat ctactatgca     240
gacactgtga cgggccgatt caccatctct agagagaatg ccaagaacac cctgtacctg     300
gaaatgagca gtctgaggtc tgaggacaca gccatgtact actgtgcaag gtatgactac     360
gataatatct ggactatgt tatggactac tggggtcaag gaacctcagt caccgtctcc     420
tcagccaaaa caacaccccc atcagtctat ccactg                                456

<210> SEQ ID NO 60
<211> LENGTH: 152
<212> TYPE: PRT
<213> ORGANISM: Mus musculus

<400> SEQUENCE: 60

Met Asp Phe Gly Leu Ser Leu Leu Ile Phe Val Leu Ile Leu Lys Gly
1               5                   10                  15

Val Gln Cys Glu Val Lys Leu Val Glu Ser Gly Gly Gly Leu Val Gln
            20                  25                  30

```
Pro Gly Gly Ser Arg Lys Leu Ser Cys Ala Ala Ser Gly Phe Thr Phe
             35                  40                  45

Ser Asp Tyr Gly Met Ala Trp Val Arg Gln Ala Pro Gly Lys Gly Pro
 50                  55                  60

Glu Trp Val Ala Phe Ile Ser Asn Leu Ala Tyr Ser Ile Tyr Tyr Ala
 65                  70                  75                  80

Asp Thr Val Thr Gly Arg Phe Thr Ile Ser Arg Glu Asn Ala Lys Asn
                 85                  90                  95

Thr Leu Tyr Leu Glu Met Ser Ser Leu Arg Ser Glu Asp Thr Ala Met
            100                 105                 110

Tyr Tyr Cys Ala Arg Tyr Asp Tyr Asp Asn Ile Leu Asp Tyr Val Met
            115                 120                 125

Asp Tyr Trp Gly Gln Gly Thr Ser Val Thr Val Ser Ser Ala Lys Thr
130                 135                 140

Thr Pro Pro Ser Val Tyr Pro Leu
145                 150

<210> SEQ ID NO 61
<211> LENGTH: 432
<212> TYPE: DNA
<213> ORGANISM: Mus musculus

<400> SEQUENCE: 61
atgaagttgc ctgttaggct gttggtgctc tggattcagg aaaccaaggg tgatgttgtg      60
ctgacccaga ctccactcac tttgtcggtt accattggac aaccagcctc tatctcttgc     120
aagtcaagtc agagcctctt atatagtaat ggaaaaacct atttgaattg gttattacag     180
aggccaggcc agtctccaaa gcgcctaatc tatgtggtgt ctaaactgga ctctggagtc     240
cctgacaggt tcactggcag tggatcagga acagatttta cactgaaaat cagcagagtg     300
gaggctgagg atttgggagt ttattattgc gtgcaaggta cacattttcc attcacgttc     360
ggctcgggga caaagttgga aataaaacgg gctgatgctg caccaactgt atccatcttc     420
ccaccatcca gt                                                         432

<210> SEQ ID NO 62
<211> LENGTH: 144
<212> TYPE: PRT
<213> ORGANISM: Mus musculus

<400> SEQUENCE: 62

Met Lys Leu Pro Val Arg Leu Leu Val Leu Trp Ile Gln Glu Thr Lys
 1               5                  10                  15

Gly Asp Val Val Leu Thr Gln Thr Pro Leu Thr Leu Ser Val Thr Ile
             20                  25                  30

Gly Gln Pro Ala Ser Ile Ser Cys Lys Ser Ser Gln Ser Leu Leu Tyr
         35                  40                  45

Ser Asn Gly Lys Thr Tyr Leu Asn Trp Leu Leu Gln Arg Pro Gly Gln
 50                  55                  60

Ser Pro Lys Arg Leu Ile Tyr Val Val Ser Lys Leu Asp Ser Gly Val
 65                  70                  75                  80

Pro Asp Arg Phe Thr Gly Ser Gly Ser Gly Thr Asp Phe Thr Leu Lys
                 85                  90                  95

Ile Ser Arg Val Glu Ala Glu Asp Leu Gly Val Tyr Tyr Cys Val Gln
            100                 105                 110

Gly Thr His Phe Pro Phe Thr Phe Gly Ser Gly Thr Lys Leu Glu Ile
            115                 120                 125
```

Lys Arg Ala Asp Ala Ala Pro Thr Val Ser Ile Phe Pro Pro Ser Ser
            130                 135                 140

<210> SEQ ID NO 63
<211> LENGTH: 435
<212> TYPE: DNA
<213> ORGANISM: Mus musculus

<400> SEQUENCE: 63
atgggatgga gcggggtctt tctcttcctc ctgtcagtaa ctgaaggtgt ccactcccag    60
gttcagctgc agcagtctgg ggctgagctg gtgaggcctg gtcctcagt gaagatttcc   120 tgcaaggctt ctggctatat attcaataac tactggataa actgggtgaa gcagaggcct   180
ggtcagggtc ttgagtggat tggacagatt tatcctggag atggtgatac taactacaat   240
gggaagttca aggtaaagc cacactgact gcagacaaat cctccagcac agcctacatg    300
cagctcagca gcctaacatc tgaggactct gcggtctatt tctgtgcaag agagggatat   360
attgtttatt ggggccaagg gactctggtc actgtctctg cagccaaaac gacaccccca   420
tctgtctatc cactg                                                    435

<210> SEQ ID NO 64
<211> LENGTH: 145
<212> TYPE: PRT
<213> ORGANISM: Mus musculus

<400> SEQUENCE: 64

Met Gly Trp Ser Gly Val Phe Leu Phe Leu Leu Ser Val Thr Glu Gly
1               5                   10                  15

Val His Ser Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Ile Phe
        35                  40                  45

Asn Asn Tyr Trp Ile Asn Trp Val Lys Gln Arg Pro Gly Gln Gly Leu
    50                  55                  60

Glu Trp Ile Gly Gln Ile Tyr Pro Gly Asp Gly Asp Thr Asn Tyr Asn
65                  70                  75                  80

Gly Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Glu Gly Tyr Ile Val Tyr Trp Gly Gln Gly Thr
        115                 120                 125

Leu Val Thr Val Ser Ala Ala Lys Thr Thr Pro Pro Ser Val Tyr Pro
    130                 135                 140

Leu
145

<210> SEQ ID NO 65
<211> LENGTH: 8
<212> TYPE: PRT
<213> ORGANISM: Artificial sequence
<220> FEATURE:
<223> OTHER INFORMATION: synthetic peptide
<220> FEATURE:
<221> NAME/KEY: MOD_RES -continued

```
<222> LOCATION: (1)..(1)
<223> OTHER INFORMATION: PYRROLIDONE CARBOXYLIC ACID

<400> SEQUENCE: 65

Glu Phe Arg His Asp Ser Gly Cys
1               5
```